US012776127B2

(12) United States Patent
Miyamoto et al.

(10) Patent No.: US 12,776,127 B2
(45) Date of Patent: Oct. 27, 2026

(54) METHOD FOR DISCRIMINATING A SORTING TARGET, SORTING METHOD, SORTING APPARATUS, AND DISCRIMINATION APPARATUS

(71) Applicant: SATAKE CORPORATION, Tokyo (JP)

(72) Inventors: Tomoyuki Miyamoto, Tokyo (JP); Shinya Harada, Tokyo (JP)

(73) Assignee: SATAKE CORPORATION, Tokyo (JP)

( * ) Notice: Subject to any disclaimer, the term of this patent is extended or adjusted under 35 U.S.C. 154(b) by 562 days.

(21) Appl. No.: 18/258,938

(22) PCT Filed: Nov. 4, 2021

(86) PCT No.: PCT/JP2021/040519
§ 371 (c)(1),
(2) Date: Jun. 22, 2023

(87) PCT Pub. No.: WO2022/137822
PCT Pub. Date: Jun. 30, 2022

(65) Prior Publication Data

US 2024/0046613 A1 Feb. 8, 2024

(30) Foreign Application Priority Data

Dec. 24, 2020 (JP) ................................ 2020-214808

(51) Int. Cl.
*G06V 10/764* (2022.01)
*B07C 5/34* (2006.01)
(Continued)

(52) U.S. Cl.
CPC .......... *G06V 10/764* (2022.01); *B07C 5/3416* (2013.01); *B07C 5/342* (2013.01);
(Continued)

(58) Field of Classification Search
CPC .. G06V 10/764; G06V 10/70; G06V 2201/06; B07C 5/3416; B07C 5/3425;
(Continued)

(56) References Cited

U.S. PATENT DOCUMENTS

| | | | | |
|---|---|---|---|---|
| 2019/0364935 | A1* | 12/2019 | Tsukamoto | A23B 7/0053 |
| 2020/0084966 | A1 | 3/2020 | Corban | |
| 2020/0360969 | A1 | 11/2020 | Lien | |

FOREIGN PATENT DOCUMENTS

| | | |
|---|---|---|
| JP | 10-076233 A | 3/1998 |
| JP | 10-279060 A | 10/1998 |

(Continued)

OTHER PUBLICATIONS

JP-2002312762-A (Year: 2002).*
(Continued)

*Primary Examiner* — Ernesto A Suarez
*Assistant Examiner* — Laurence R Brothers
(74) *Attorney, Agent, or Firm* — Renner, Otto, Boisselle & Sklar, LLP

(57) ABSTRACT

A method for discriminating a sorting target includes transferring the sorting target, imaging the sorting target during the transferring, and discriminating the sorting target based on imaging information acquired in the imaging. The imaging information includes adjacency information between sorting targets, and classification information of the sorting target.

11 Claims, 7 Drawing Sheets

(51) Int. Cl.

| | |
|---|---|
| ***B07C 5/342*** | (2006.01) |
| ***B65B 57/14*** | (2006.01) |
| ***G01N 21/85*** | (2006.01) |
| ***G01N 23/04*** | (2018.01) |
| ***G01N 33/02*** | (2006.01) |
| ***G06T 7/00*** | (2017.01) |
| ***G06V 10/70*** | (2022.01) |

(52) U.S. Cl.
CPC .......... *B07C 5/3425* (2013.01); *G01N 23/04* (2013.01); *G01N 33/02* (2013.01); *G06T 7/0004* (2013.01); *G06V 10/70* (2022.01); *B65B 57/14* (2013.01); *G01N 2021/8592* (2013.01); *G01N 2223/652* (2013.01); *G06T 2207/10116* (2013.01); *G06T 2207/20081* (2013.01); *G06T 2207/30128* (2013.01); *G06T 2207/30161* (2013.01); *G06V 2201/06* (2022.01)

(58) Field of Classification Search
CPC .......... B07C 5/342; G06T 2207/20081; G06T 7/0004; G06T 2207/30128; G06T 2207/10116; G06T 2207/30161; B65B 57/14; G01N 2021/8592; G01N 2223/652; G01N 33/02; G01N 23/04
See application file for complete search history.

(56) References Cited

FOREIGN PATENT DOCUMENTS

| | | | | |
|---|---|---|---|---|
| JP | 2000-237696 | A | | 9/2000 |
| JP | 2002-039731 | A | | 2/2002 |
| JP | 2002-062113 | A | | 2/2002 |
| JP | 2002-062126 | A | | 2/2002 |
| JP | 2002312762 | A | * | 10/2002 |
| JP | 2004-301690 | A | | 10/2004 |
| JP | 2005-055245 | A | | 3/2005 |
| JP | 2005-083775 | A | | 3/2005 |
| JP | 2005-091159 | A | | 4/2005 |
| JP | 2006-064662 | A | | 3/2006 |
| JP | 2007-198394 | A | | 8/2007 |
| JP | 2015-161522 | A | | 9/2015 |
| JP | 2015-529154 | A | | 10/2015 |
| JP | 2019-023664 | A | | 2/2019 |
| JP | 2020-012741 | A | | 1/2020 |
| WO | 2018/131685 | A1 | | 7/2018 |

OTHER PUBLICATIONS

Extended European Search Report for corresponding Application No. EP 21 909 977.7, issued Apr. 22, 2024.
Office Action for corresponding Application No. JP2022-571934, issued Jan. 23, 2024, with English translation.
International Search Report corresponding to International Application No. PCT/JP2021/040519 mailed Jan. 11, 2022, including English translation.
Written Opinion corresponding to International Application No. PCT/JP2021/040519 mailed Jan. 1, 2022, Japanese only.
Office Action issued by the Chinese National Intellectual Property Administration for corresponding Chinese National Phase application No. 202180086319.9, issued Jun. 19, 2025.
English language translation of the International Preliminary Report on Patentability corresponding to International Application No. PCT/JP2021/040519 issued Jun. 13, 2023.
Office Action issued for corresponding Chinese National Phase Application No. 202180086319.9, mailed Nov. 14, 2025.
Office Action issued for corresponding European National Phase Application No. 21909977.7, mailed Oct. 6, 2025.
Office Action issued for corresponding Chinese National Phase Application No. 202180086319.9, mailed Feb. 9, 2026.

* cited by examiner

METHOD FOR DISCRIMINATING A SORTING TARGET, SORTING METHOD, SORTING APPARATUS, AND DISCRIMINATION APPARATUS

This application is a national phase of International Application No. PCT/JP2021/040519 filed Nov. 4, 2021, which claims the priority of Japanese Patent Application JP 2020-214808 filed Dec. 24, 2020, both of which are hereby incorporated herein by reference in their entireties.

TECHNICAL FIELD

The present disclosure relates to a discrimination method when a sorting target is sorted. Further, the present disclosure relates to a sorting method and a sorting apparatus that sort the sorting target based on this method for discriminating the sorting target.

BACKGROUND

Conventionally, there have been known various techniques for discriminating and sorting a foreign object mixed in inspection targets such as food or industrial products and techniques for discriminating and sorting inspection targets themselves based on a predetermined condition. Hereinafter, at least one of an inspection target and a foreign object targeted for at least one of discrimination and sorting will be referred to as a sorting target.

In recent years, techniques using a captured image have been proposed as techniques for, for example, sorting a sorting target. One known example is a technique of performing processing for sorting a sorting target as appropriate by, for example, irradiating the sorting target with light and measuring an absorption spectrum of reflected light with respect to visible light and near-infrared light to remove a foreign object and an impurity mixed in food such as fruits (Japanese Patent Application Laid-Open No. 2004-301690).

More specifically, the conventional technique according to Japanese Patent Application Laid-Open No. 2004-301690 first measures the absorption spectrum of the reflected light with respect to visible light and near-infrared light that is acquired by irradiating the sorting target (food, and a foreign object and the like contained in the food) with the light. Next, this technique performs quadratic differential processing on the absorption spectrum, and measures a wavelength band exhibiting a difference in quadratic differential spectrum between the food, and a foreign object and the like other than food. Then, the technique generates a quadratic differential spectroscopic image of the above-described wavelength band with respect to the food, thereby allowing a foreign object and the like contained in this food to be detected.

SUMMARY

However, the above-described conventional technique (Japanese Patent Application Laid-Open No. 2004-301690) has involved a problem of having difficulty in discriminating and sorting inspection targets (food substances in Japanese Patent Application Laid-Open No. 2004-301690) from each other based on a predetermined condition, although having been able to sort the inspection target set as the sorting target, and a foreign object and the like other than that.

Further, the above-described technique has had difficulty in perceiving the state of the inspection target itself set as the sorting target. More specifically, there has been such a problem that, even when the inspection target has had to be, for example, discriminated based on the surface state or the like of the inspection target, the above-described conventional technique has failed to accurately perceive the surface state or the inner state (a defective product containing an invisible shape, a shape abnormality, and the like) of the inspection target, thereby having difficulty in discriminating and sorting the inspection target based on them.

In light thereof, the present disclosure has been contrived to solve the problems with the above-described conventional technique, and an object thereof is to provide a method for discriminating a sorting target that appropriately perceives a state of the sorting target itself and a relationship between a plurality of sorting targets and appropriately discriminates the sorting target based on this perceived information.

Further, the present disclosure has been contrived to solve the problems with the above-described conventional technique, and an object thereof is to provide a method and an apparatus for sorting a sorting target that appropriately perceive a state of the sorting target itself and a relationship between a plurality of sorting targets and appropriately discriminate and sort the sorting target based on this perceived information.

According to a first aspect of the present disclosure, a method for discriminating a sorting target includes transferring the sorting target, imaging the sorting target during the transferring, and discriminating the sorting target based on imaging information acquired in the imaging. The imaging information includes adjacency information between sorting targets, and classification information of the sorting target.

As will be used herein, "imaging" refers to forming an image of a condition (an external and/or internal condition) of a target (sorting target) using an optical method by irradiating the target with an electromagnetic wave and receiving (detecting) at least one of a reflected signal (reflected light) and a transmitted signal (transmitted light) thereof to perceive the condition of the target such as the external condition and/or the internal condition of the target. Further, the "electromagnetic wave" refers to a wave that propagates a change in an electric field and a magnetic field, and light and a radio wave are one type of electromagnetic wave. The imaging means that performs the "imaging" includes an electromagnetic wave generator (for example, an X-ray generator) configured to emit the electromagnetic wave, and an electromagnetic wave detector (for example, an X-ray detector) configured to receive at least one of the transmitted signal and a reflected signal of the emitted electromagnetic wave.

Further, the "adjacency information" refers to information assigned according to a distance between adjacent sorting targets (an adjacency distance) or an adjacency ratio (a ratio of the distance between sorting targets to the size of the sorting targets), and is formed by, for example, assigning predetermined information (for example, color information) different from the sorting target, the background, and the like to at least one of a portion where sorting targets are in contact with each other, a portion where the distance between sorting targets is a predetermined distance or shorter, and a portion where the adjacency ratio between sorting targets is a predetermined ratio or lower.

Further, the "classification information" refers to information assigned according to the state of the sorting target, and examples thereof include "acceptable portion information", which is an acceptable portion of the sorting target, and "defective portion information", which is a defective portion such as a missing portion or an interior appearance defective portion of the sorting target. In a case where there is a plurality of types of information such as the "acceptable portion information" and the "defective portion information" as the "classification information", these types of "classification information" are formed by assigning individually different pieces of information (for example, the color information), respectively.

According to a second aspect of the present disclosure, a method for discriminating a sorting target includes transferring the sorting target, imaging the sorting target during the transferring, and discriminating the sorting target based on imaging information acquired in the imaging. The imaging information includes adjacency information between sorting targets, classification information of the sorting target, and background information of the sorting target.

According to a third aspect of the present disclosure, a method for discriminating a sorting target includes transferring the sorting target, imaging the sorting target during the transferring, and discriminating the sorting target based on imaging information acquired in the imaging. The discriminating is performed using an inference model generated based on learning information regarding the sorting target, and the learning information includes the adjacency information between the sorting targets and the classification information of the sorting target. The discriminating includes discriminating the sorting target using the imaging information and the inference model.

The "inference model" can be acquired using a system (a learning program) formed by combining at least one or more of a support vector machine (SVM), a naive Bayes classifier, logistic regression, a random forest, a neural network, deep learning, the k-nearest neighbors algorithm, AdaBoost, bagging, C4.5, the kernel method, stochastic gradient descent, Lasso regression, Ridge regression, Elastic Net, the interpolation method, and collaborative filtering. More specifically, the "inference model" capable of implementing the discrimination process according to the present disclosure can be acquired by causing such a system (the learning program) to learn predetermined image information (the learning information and/or a learning image). Hereinafter, the same concept shall also apply when the term "inference model" is simply stated.

Further, the method for discriminating the sorting target according to the third aspect may be configured in such a manner that the learning information includes the adjacency information between the sorting targets, the classification information of the sorting target, and background information of the sorting target.

According to a fourth aspect of the present disclosure, a sorting method includes transferring a sorting target, imaging the sorting target during the transferring, discriminating the sorting target based on imaging information acquired in the imaging, and sorting the sorting target based on discrimination information acquired in the discriminating. The imaging information includes adjacency information between sorting targets, and classification information of the sorting target.

Further, the sorting method according to the present aspect may be configured in such a manner that the imaging information includes the adjacency information between the sorting targets, the classification information of the sorting target, and background information of the sorting target.

According to a fifth aspect of the present disclosure, a sorting method includes transferring a sorting target, imaging the sorting target during the transferring, discriminating the sorting target based on imaging information acquired in the imaging, and sorting the sorting target based on discrimination information acquired in the discriminating. The discriminating is performed using an inference model generated based on learning information regarding the sorting target, and the learning information includes adjacency information between sorting targets, and classification information of the sorting target. The discriminating includes discriminating the sorting target using the imaging information and the inference model.

Further, the method for sorting the sorting target according to the fifth aspect may be configured in such a manner that the learning information includes the adjacency information between the sorting targets, the classification information of the sorting target, and background information of the sorting target.

According to a sixth aspect of the present disclosure, a sorting apparatus includes a transfer means configured to transfer a sorting target, an imaging means configured to image the sorting target during the transfer by the transfer means, a discrimination means configured to discriminate the sorting target based on imaging information acquired by the imaging means, and a sorting means configured to sort the sorting target based on discrimination information acquired by the discrimination means. The imaging information includes adjacency information between sorting targets, and classification information of the sorting target.

Further, the sorting apparatus according to the present aspect may be configured in such a manner that the imaging information includes the adjacency information between the sorting targets, the classification information of the sorting target, and background information of the sorting target.

According to a seventh aspect of the present disclosure, a sorting apparatus includes a transfer means configured to transfer a sorting target, an imaging means configured to image the sorting target during the transfer by the transfer means, a discrimination means configured to discriminate the sorting target based on imaging information acquired by the imaging means, and a sorting means configured to sort the sorting target based on discrimination information acquired by the discrimination means. The discrimination means includes an inference model generated based on learning information regarding the sorting target, and the learning information includes adjacency information between sorting targets, and classification information of the sorting target. The discrimination means is further configured to discriminate the sorting target using the imaging information and the inference model.

The "imaging means" includes an electromagnetic wave generator (for example, an X-ray generator) configured to emit an electromagnetic wave, and an electromagnetic wave detector (for example, an X-ray detector) configured to detect at least one of transmission information (transmitted light or a transmitted signal) and reflection information (reflected light or a reflected signal) of the emitted electromagnetic wave.

Further, the apparatus for sorting the sorting target according to the seventh aspect may be configured in such a manner that the learning information includes the adjacency information between the sorting targets, the classification information of the sorting target, and background information of the sorting target.

According to the present disclosure, it is possible to provide a method for discriminating a sorting target that appropriately perceives a state of the sorting target itself and a relationship between a plurality of sorting targets and appropriately discriminates the sorting target based on this perceived information.

Further, according to the present disclosure, it is possible to provide a method and an apparatus for sorting a sorting target that appropriately perceive a state of the sorting target itself and a relationship between a plurality of sorting targets and appropriately discriminate and sort the sorting target based on this perceived information.

DETAILED DESCRIPTION OF THE EMBODIMENTS

In the following description, a method for discriminating a sorting target, a method for sorting the sorting target, an apparatus for sorting the sorting target, and the like according to embodiments of the present disclosure will be described with reference to the drawings.

Now, examples of the "sorting target" include a granular object, such as nuts, beans, a kernel, a resin, a stone, a glass piece, and a wood material. Further, the "kernel" refers to a grain piece, and the grain is one of generic terms indicating food acquired from plants. Examples of the grain include rice, wheat, foxtail millet, Japanese millet, corn, soybean, red bean, and buckwheat.

Figure 1:
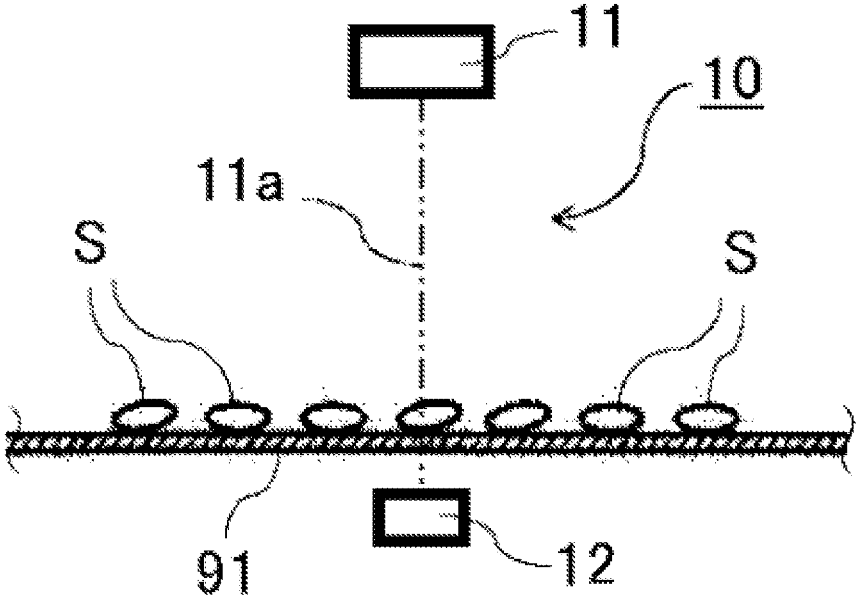
FIG. 1 illustrates a partial schematic view of an apparatus for sorting a sorting target according to an embodiment of the present disclosure (a schematic side view of an X-ray discriminator).
Figure 2:
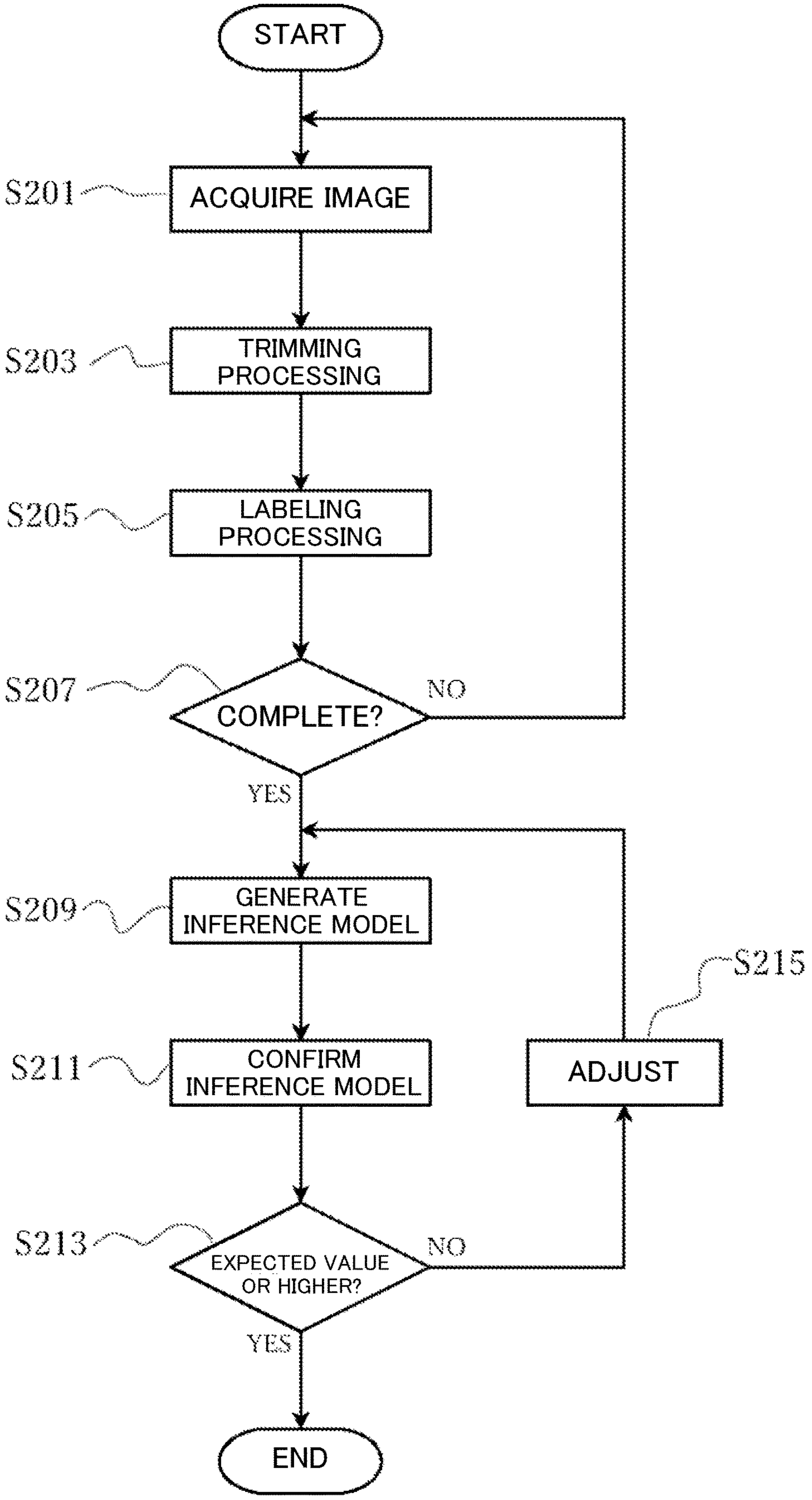
FIG. 2 illustrates a flowchart regarding a method for constructing an inference model used by an X-ray sorter (the X-ray discriminator included therein) according to an embodiment of the present disclosure.
Figure 3A:
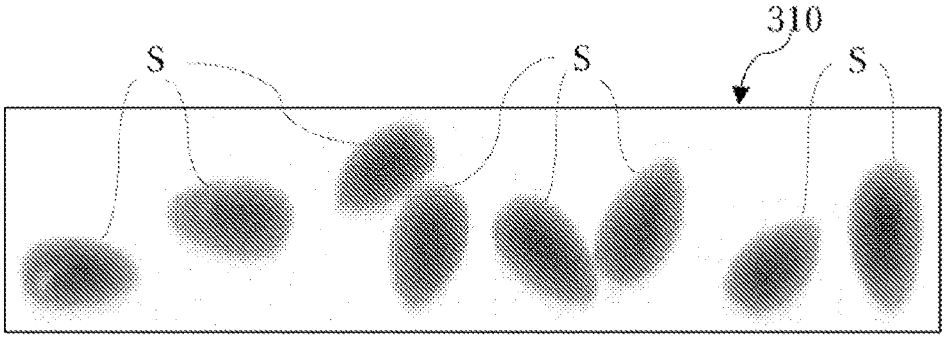
FIG. 3A is a schematic view of imaging information and the like in the method for constructing the inference model used by the X-ray sorter (the X-ray discriminator included therein) according to an embodiment of the present disclosure, and illustrates a raw image acquired by irradiating the sorting target with X-ray.
Figure 3B:
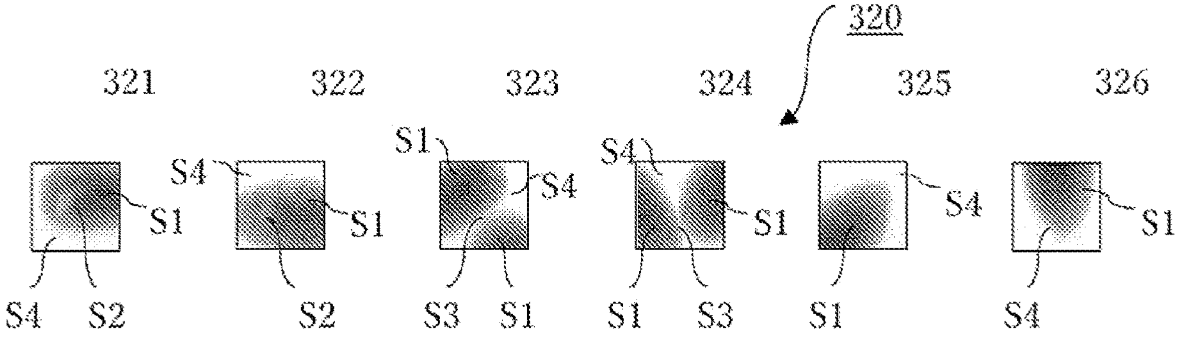
FIG. 3B is a schematic view of imaging information and the like in the method for constructing the inference model used by the X-ray sorter (the X-ray discriminator included therein) according to the embodiment of the present disclosure, and illustrates trimmed images (a trimmed image group) acquired by performing trimming processing from the acquired raw image to generate learning images.
Figure 3C:
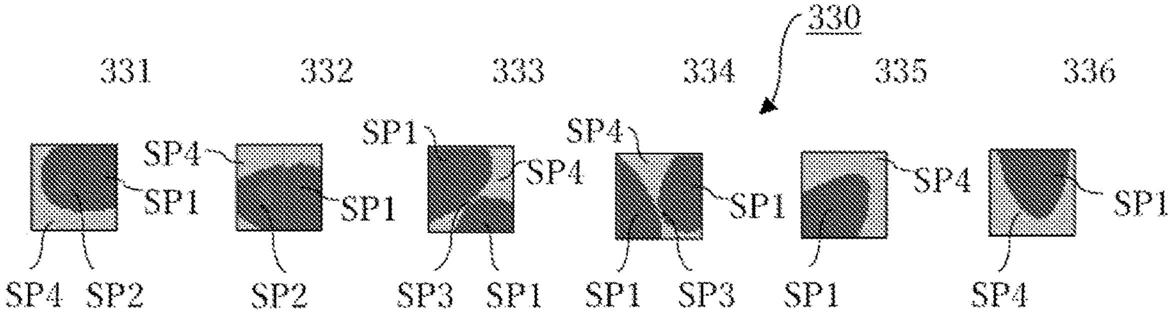
FIG. 3C is a schematic view of imaging information and the like in the method for constructing the inference model used by the X-ray sorter (the X-ray discriminator included therein) according to the embodiment of the present disclosure, and illustrates labeling images (a labeling image group) acquired by performing labeling processing with respect to an acceptable portion (acceptable portion information and classification information), a defective portion (defective portion information and the classification information), an adjacency portion (adjacency information), and a background portion (background information) based on the trimmed images.
Figure 4:
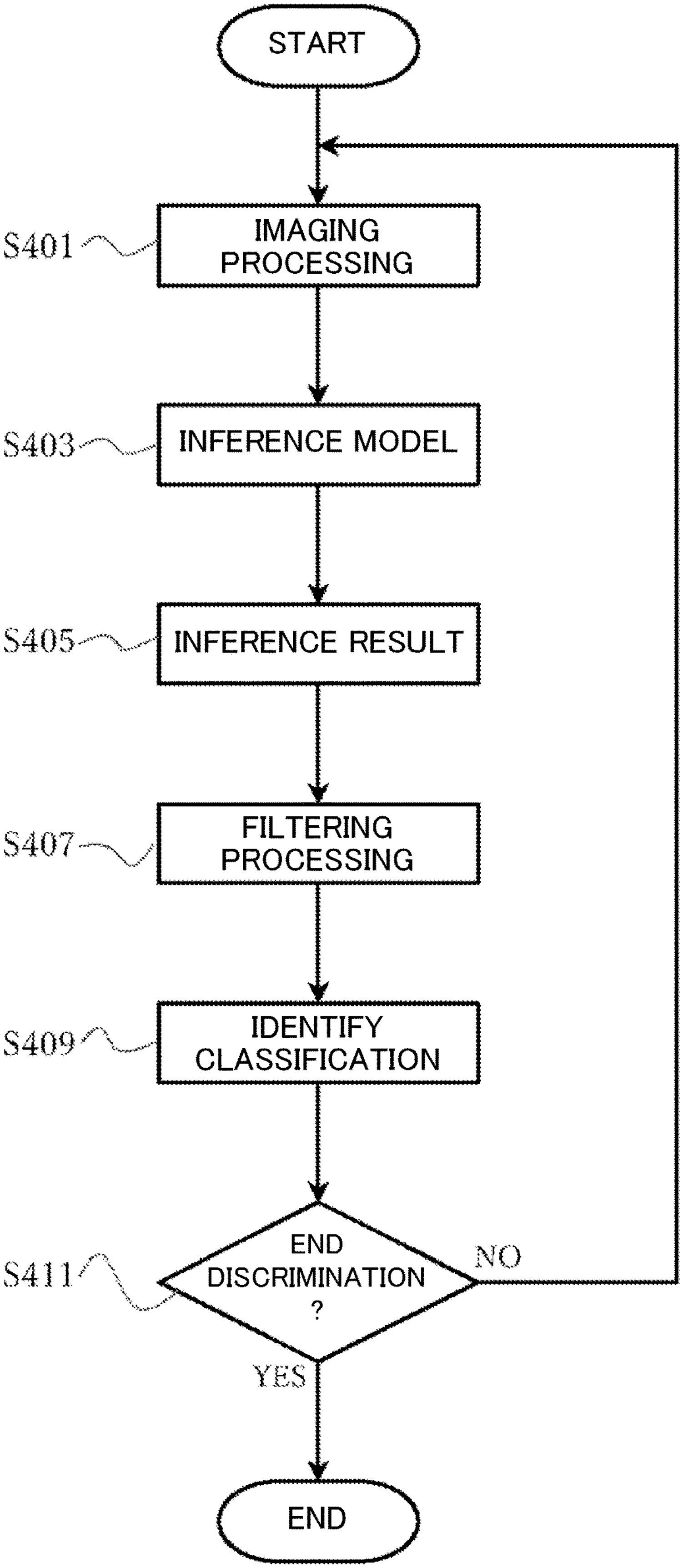
FIG. 4 illustrates a flowchart regarding a discrimination process (a method for discriminating the sorting target) performed using the X-ray sorter (the X-ray discriminator included therein) according to an embodiment of the present disclosure.
Figure 5A:
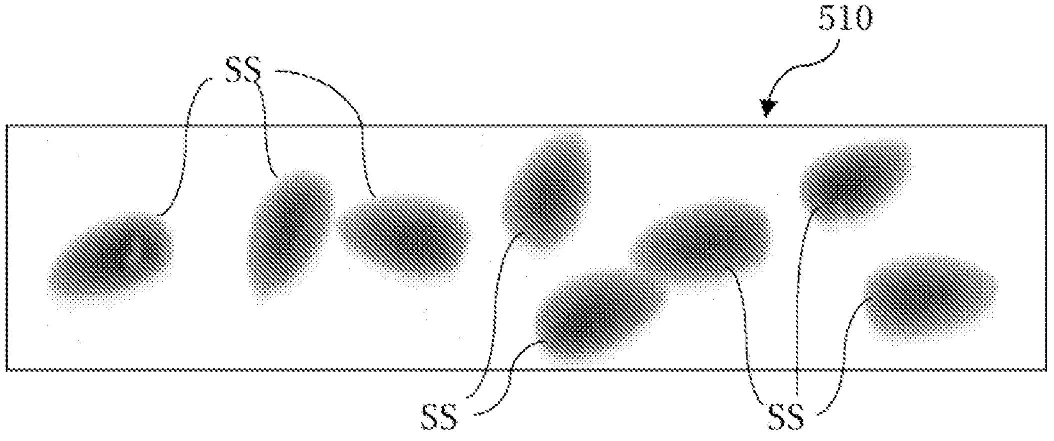
FIG. 5A is a schematic view of, imaging information and the like at the time of the discrimination process performed using the X-ray sorter (the X-ray discriminator included therein) according to an embodiment of the present disclosure, and illustrates a raw image captured while the sorting target is irradiated with X-ray.
Figure 5B:
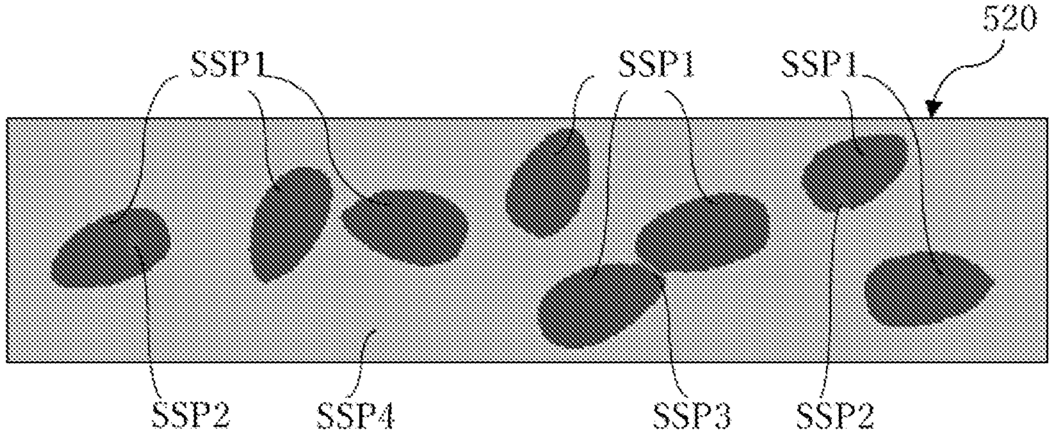
FIG. 5B is a schematic view of imaging information and the like at the time of the discrimination process performed using the X-ray sorter (the X-ray discriminator included therein) according to an embodiment of the present disclosure, and illustrates an inference result image acquired when the inference model is applied to the captured raw image (after an inference is made using the inference model).
Figure 5C:
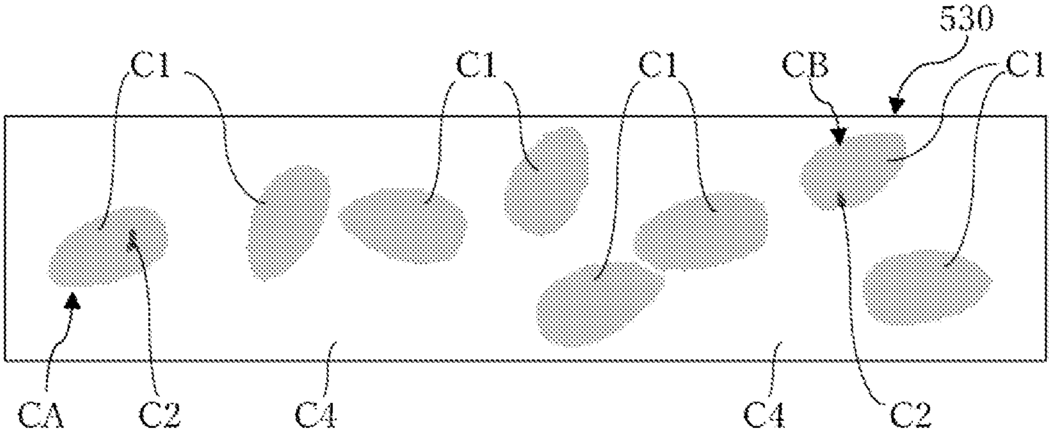
FIG. 5C is a schematic view of imaging information and the like at the time of the discrimination process performed using the X-ray sorter (the X-ray discriminator included therein) according to an embodiment of the present disclosure, and illustrates a post-filter processing image acquired when the inference result image is filtered.

<First Embodiment> FIG. 1 illustrates a partial schematic view (a partial schematic side view) of an apparatus for sorting a sorting target according to an embodiment of the present disclosure. More specifically, FIG. 1 illustrates a schematic view (a schematic side view) of an X-ray discriminator 10, which is a part of the sorting apparatus. Further, FIG. 2 illustrates a flowchart regarding a method for constructing an inference model used by an X-ray sorter according to the present embodiment. Further, FIGS. 3A to 3C illustrate schematic views of imaging information and the like used at the time of the construction of the inference model according to the present embodiment. FIG. 3A illustrates a raw image acquired by irradiating the sorting target with an electromagnetic wave (an X-ray). FIG. 3B illustrates trimmed images (a trimmed image group) acquired by performing trimming processing from the acquired raw image to generate learning images (one non-limiting example of "learning information" in the claims). FIG. 3C illustrates labeling images (a labeling image group) acquired by performing labeling processing with respect to an acceptable portion (acceptable portion information as one example of classification information), a defective portion (defective portion information as one example of the classification information), an adjacency portion (adjacency information), and a background portion (background information) based on the trimmed images. In the embodiment according to the present disclosure, the labeling images are used as the learning images (the learning information). Further, FIG. 4 illustrates a flowchart regarding a discrimination process (the method for discriminating the sorting target) performed using the X-ray sorter (the X-ray discriminator included therein) according to the present embodiment. Further, FIGS. 5A to 5C illustrate schematic views of imaging information and the like at the time of the discrimination process performed using the X-ray discriminator according to the present embodiment. FIG. 5A illustrates a raw image captured by irradiating the sorting target with an X-ray. FIG. 5B illustrates an inference result image acquired when the inference model is applied to the captured raw image. FIG. 5C illustrates a post-filter processing image acquired when the inference result image is filtered.

As illustrated in FIG. 1, the X-ray discriminator 10 forming the sorting apparatus according to the present disclosure includes an X-ray generation portion 11 (an electromagnetic wave generation portion), which irradiates a sorting target S on a conveyance path 91 with X-ray 11*a*, and an X-ray detection portion 12 (an electromagnetic wave detection portion), which detects the X-ray 11*a* emitted from the X-ray generation portion 11. In addition to the X-ray generation portion 11 and the X-ray detection portion 12, the X-ray discriminator 10 according to the present embodiment includes a partition wall provided so as to cover the X-ray generation portion 11 and the like, various controllers such as an image processor connected to each of them, other components, and the like, although they are omitted in this FIG. 1.

Further, the X-ray discriminator 10 according to the present embodiment is configured in such a manner that the sorting target S moves through between the X-ray generation portion 11 and the X-ray detection portion 12 due to driving of the conveyance path 91 or an inclination of the conveyance path 91 at a predetermined angle. In other words, the X-ray discriminator 10 according to the present embodiment is configured to be able to transfer the sorting target S in a predetermined direction (a leftward direction or a rightward direction in FIG. 1) through between the X-ray generation portion 11 and the X-ray detection portion 12. A process of transferring the sorting target S in this manner is one non-limiting example of "transferring" in the claims. The "transferring or transfer process" in the present disclosure is a concept that contains not only a state in which the sorting target S is transferred by a belt or the like but also a state in which the sorting target S is transferred by being ejected into the air depending on circumstances.

In the present embodiment, the X-ray discriminator 10 illustrated in FIG. 1 may function as a part of a machine learning apparatus when the inference model installed in the sorting apparatus is constructed, along with constituting a part of the sorting apparatus. In the following description, first, for example, a method for constructing the inference model installed in the sorting apparatus (the X-ray discriminator 10 thereof) according to the present embodiment will be described.

The machine learning apparatus in the case where the inference model according to the present embodiment is constructed includes the X-ray discriminator 10, a personal computer (hereinafter also referred to as a "PC") (not illustrated), and the like. The PC includes an arithmetic processing unit (equipped with an arithmetic unit, a control unit, a clock, a register, and the like) such as a CPU (central processing unit) or a GPU (graphics processing unit), a memory, an input/output device, a bus (a signal circuit), and the like.

The machine learning apparatus used when the inference model according to the present embodiment is constructed includes the PC and the like as described above, and this PC is provided with a learning program formed by combining at least one or more of a support vector machine (SVM), a naive Bayes classifier, logistic regression, a random forest, a neural network, deep learning, the k-nearest neighbors algorithm, AdaBoost, bagging, C4.5, the kernel method, stochastic gradient descent, Lasso regression, Ridge regression, Elastic Net, the interpolation method, and collaborative filtering. In the present embodiment, the learning program is formed mainly based on deep learning by way of example.

In the present embodiment, at least one of imaging information (an acquired image) acquired using the X-ray discriminator 10 and image information resulting from appropriately processing this imaging information (the acquired image) is used as a learning image, and the inference model is constructed using this learning image and the learning program. In the following description, the method for constructing the inference model will be described with reference to FIGS. 1 to 3C. As described above, FIG. 2 illustrates the flowchart regarding the method for constructing the inference model used by the X-ray sorter according to the present embodiment. FIGS. 3A to 3C illustrate schematic views of the imaging information (the acquired image) and the like used when the inference model according to the present embodiment is constructed.

As illustrated in FIG. 2, when the inference model according to the present embodiment is constructed, an image (an X-ray transmission image) regarding the sorting target S on the conveyance path 91 is acquired using the X-ray discriminator 10 (an image acquisition process: step S201). In the present embodiment, in this image acquisition process S201, a line-shaped raw image 310 is acquired regarding a plurality of sorting targets S on the conveyance path 91 (refer to FIG. 3A). More specifically, in step S201, image information corresponding to the predetermined number of lines (for example, 512 lines) is acquired from the X-ray detection portion 12, and this image information (the raw image 310) is confirmed to contain the sorting target S imaged therein based on a predetermined threshold value and is appropriately stored into the memory.

Next, in the present embodiment, trimming processing is performed on a predetermined portion of the raw image 310 acquired in the image acquisition process S201 (a trimming processing process: step S203). In other words, in this step S203, a trimmed image group 320 (a first trimmed image 321 to a sixth trimmed image 326) is generated from the raw image 310 (refer to FIG. 3B). In this trimming processing process S203, the trimming processing is performed so as to bring each of the trimmed images into a state of containing the sorting target S therein.

In the present embodiment, this step S203 (the trimming processing process) includes cutting out and extracting an image(s) containing acceptable portion information S1 (the classification information), defective portion information S2 (the classification information), and background information S4 of the sorting target S (the first trimmed image 321 and the second trimmed image 322), an image(s) containing the acceptable portion information S1, adjacency information S3, and the background information S4 of the sorting target S (the third trimmed image 323 and the fourth trimmed image 324), and an image(s) containing the acceptable portion information S1 and the background information S4 of the sorting target S (the fifth trimmed image 325 and the sixth trimmed image 326).

In this trimming processing process S203, the images are cut out and extracted so as to bring the images into a state of containing at least two or more types of information (for example, a state of containing the acceptable portion information S1, the defective portion information S2, and the background information S4 (the first trimmed image 321 and the like), a state of containing the acceptable portion information S1, the adjacency information S3, and the background information S4 (the third trimmed image 323 and the like), or a state of containing the acceptable portion information S1 and the background information S4 (the fifth trimmed image 325 and the like)).

In the present embodiment, the trimming processing process S203 is performed so as to maintain, at a predetermined ratio, the acceptable portion information S1, which is an acceptable portion of the sorting target S (a portion of the sorting target S that excludes a defective portion such as a missing portion or an interior appearance defective portion (an internal invisible shape)), and the defective portion information S2, which is a defective portion such as a missing portion or an interior appearance defective portion of the sorting target S. The acceptable portion information S1 and defective portion information S2 are one non-limiting example of the "classification information."

Further, in the present embodiment, the trimming processing process S203 is performed so as to maintain, at a predetermined ratio, a portion where sorting targets S are in contact with each other and a portion where a distance between adjacent sorting targets S (an adjacency distance) or an adjacency ratio (a ratio of the distance between sorting targets S to the size of the sorting targets S) is equal to or smaller than a predetermined value. For example, at least one of the portion where sorting targets S are in contact with each other, the portion where the distance between sorting targets S is a predetermined distance or shorter, and the portion where the adjacency ratio between sorting targets S is a predetermined ratio or lower is one non-limiting example of the "adjacency information".

Further, in the present embodiment, the trimming processing process S203 is performed so as to establish a predetermined ratio between the classification information, the adjacency information, and the background information.

The trimming size in the trimming processing process (S203) according to the present embodiment is determined according to the size (the projection area of the body) and/or the shape of the sorting target S.

More specifically, the trimming processing is performed according to a size approximately equal to the size of a single body of the sorting target S. At this time, in a case where the sorting target S has a shape close to a "circle" or a "square", the trimming processing is performed to trim the image into a size approximately equal to or slightly larger than the size (area) of an average single body of this sorting target S ("the average value of a single body−5% or so"≤the trimming size≤"the average value of a single body+15% or so"). Alternatively, in a case where the sorting target S has a shape close to an "ellipse" or a "rectangle", the trimming processing is performed to trim the image into a size approximately equal to or slightly smaller than the size of an average single body of this sorting target S ("the average value of a single body−15% or so"≤the trimming size≤"the average value of a single body+5% or so").

For example, in the present embodiment, if the sorting target S is an almond, the trimming processing is performed according to a size of 40×40 pixels (a size approximately equal to or slightly smaller than the size of an average single body).

Further, in the present embodiment, after the trimming processing process (S203), normalization processing is performed on each of the trimmed images. However, the timing of this normalization processing is not limited to the timing after the trimming processing process (S203), and, for example, the normalization processing may be performed on the raw image 310 after the image acquisition process (S201), and the trimming processing process may be performed on the image resulting from this normalization processing. Examples performed as the "normalization processing" include a shading correction for evening out a variation in light quantity or the sensitivity of an element in the detection portion, or a conversion of the image for keeping a tone value acquired according to electromagnetic wave intensity within a predetermined range. For example, in the present embodiment, the normalization processing is performed so as to keep the range of a tone value acquired according to electromagnetic wave intensity within a range of 0 to 1.

Next, in the present embodiment, labeling processing is performed using the trimmed image group 320 generated in the trimming processing process S203 (the trimmed image group after the normalization processing) (a labeling processing process: step S205). In other words, in this labeling processing process S205, a labeling image group 330 (a first labeling image 331 to a sixth labeling image 336) (one non-limiting example of the "learning information" in the claims) is generated from the trimmed image group after the normalization processing (refer to FIG. 3C).

In the present embodiment, in the step S205 (the labeling processing process), what is imaged (which information is contained) is determined with respect to all pixels forming each image based on each of the trimmed images 321 to 326 in the trimmed image group 320 (each of the trimmed images after the normalization processing), and any of an acceptable portion labeling portion SP1 (one non-limiting example of the "classification information" in the claims), a defective portion labeling portion SP2 (corresponding to the "classification information" in the present invention), an adjacency labeling portion SP3 (one non-limiting example of the "adjacency information" in the claims), and a background labeling portion SP4 (one non-limiting example of the "background information" in the claims) is assigned.

The "classification information" in the present embodiment is information assigned according to the state of the sorting target S, and the acceptable portion labeling portion SP1 and the defective portion labeling portion SP2 in the present embodiment correspond to the classification information. Further, the adjacency labeling portion SP3 corresponds to the adjacency information, and the background labeling portion SP4 corresponds to the background information.

The adjacency labeling portion SP3 (the adjacency information) assigned in the labeling processing process S205 according to the present embodiment is information assigned according to the distance between adjacent sorting targets S (the adjacency distance) or the adjacency ratio (the ratio of the distance between sorting targets S to the size of the sorting targets S). The adjacency labeling portion SP3 (the adjacency information) is assigned to, for example, at least one of the portion where sorting targets S are in contact with each other, the portion where the distance between sorting targets S is the predetermined distance or shorter, and the portion where the adjacency ratio between sorting targets S is the predetermined ratio or lower. Now, in the present embodiment, for example, a portion where adjacent sorting targets S are determined to be connected to each other when being binarized based on some predetermined value is defined as the adjacency labeling portion SP3 (the adjacency information).

Further, in the labeling processing process S205 according to the present embodiment, respective criteria for determining the labeling are, for example, defined in the following manner.

Specifically, brightness of an acquired signal is used as the criteria for determining the labeling.

In the present embodiment, for example, a plurality of brightness reference values (a first labeling reference value and a second labeling reference value) are set, and the labeling processing is performed based on these brightness reference values. In the present example, the second labeling reference value is defined to be a brighter value than the first labeling reference value.

In the present embodiment, for example, the acceptable portion labeling portion SP1 is assigned to a portion having brightness equal to or lower than the first labeling reference value (a dark portion), and the background labeling portion SP4 is assigned to a portion having brightness equal to or higher than the second labeling reference value (a bright portion) using the above-described first labeling reference value and second labeling reference value. Further, the defective portion labeling portion SP2 is assigned to a portion having predetermined brightness (predetermined brightness between the first labeling reference value and the second labeling reference value) in a region having brightness equal to or lower than the first labeling reference value, and a portion having predetermined brightness that exists between the portion having brightness equal to or lower than the first labeling reference value and the portion having brightness equal to or higher than the second labeling reference value. Further, the adjacency labeling portion SP3 is assigned to a portion darker than the second labeling reference value that is a region where a plurality of regions having brightness equal to or lower than the first labeling reference value are in proximity to or in contact with each other.

This means that, in the present embodiment, each of the labeling images 331 to 336 in the labeling image group 330 is subjected to the assignment of the four labels (the labeling portions SP1 to SP4) to all of the pixels forming each of the images based on the above-described determination criteria as illustrated in FIG. 3C. The labeling images 331 to 336 generated in this step S205 are appropriately stored into a predetermined memory as the learning images (the learning information).

In this labeling processing process S205, for example, a hollow portion of the sorting target S is recognized as a defective portion (an interior appearance defective portion) and is subjected to the labeling processing as a defective portion (the defective portion labeling portion SP2 is formed). Then, a portion other than the defective portion of the sorting target S is subjected to the labeling processing as an acceptable portion (the acceptable portion labeling portion SP1 is formed).

Next, in the present embodiment, whether to complete the labeling processing process S205 is determined based on a predetermined condition (a completion determination process: step S207).

One possible example of the "predetermined condition" at this time is to employ at least one of, for example, the total number of labeling images on which the labeling processing is completed, the total number of pixels in the labeling images on which the labeling processing is completed, the sum of the number of pixels in the acceptable portion labeling portion and the number of pixels in the defective portion labeling portion in the labeling images or the respective percentages thereof, and the sum of the number of pixels in the classification information, the number of pixels in the adjacency information, and the number of pixels in the background information in the labeling images or the respective percentages thereof. This "predetermined condition" may be one of the above-described conditions or may be a combination of a plurality of conditions selected from the above-described conditions.

In the completion determination process S207 according to the present embodiment, whether to complete the labeling processing process S205 is determined based on, for example, whether the labeling processing is completed on the predetermined number of labeling images or more (for example, 500 images or more) and the ratio of the numbers in these labeling images matches a predetermined ratio (for example, a ratio "the number of images having (SP1+SP4): the number of images having (SP1+SP2+SP4):the number of images having (SP1+SP2+SP3)=(60±10%):(25±10%):(15±10%)").

If it is determined to complete the labeling processing process S205 based on the predetermined condition in the completion determination process S207 (if "YES" is determined in S207), next, processing in and after step S209 is performed. If it is determined not to complete the labeling processing process S205 based on the predetermined condition (if "NO" is determined in S207), the processing in and after step S201 is repeatedly performed.

If it is determined to complete the labeling processing process S205 in the completion determination process S207 according to the present embodiment (if "YES" is determined in S207), next, processing for generating the inference model is performed using the labeling images and the like (an inference model generation process: step S209).

In the inference model generation process S209 according to the present embodiment, the inference model is generated by conducting deep learning based on the labeling images (the learning images or the learning information) stored in the memory (reading the labeling images into the PC and conducting machine learning according to the learning program).

The number of labeling images used at the time of this generation of the inference model (for example, the images 331 to 336 labeled pixel by pixel (labeled with any label of the four labels SP1 to SP4)) is, for example, 500 images or more, and the ratio of the numbers in these labeling images matches, for example, the ratio "the number of images having (SP1+SP4):the number of images having (SP1+SP2+SP4):the number of images having (SP1+SP2+SP3)=60%: 25%: 15%."

Next, in the present embodiment, confirmation processing is performed with respect to the inference model generated in the inference model generation process S209 (an inference model confirmation process: step S211). In the inference model confirmation process S211, for example, inference processing using the generated inference model is performed on the raw image 310 from which the labeling images used at the time of the generation of the inference model are originated, and an accuracy is calculated by comparing a result of this inference and the learning information, as one method. Alternatively, for example, in the inference model confirmation process S211, a test image different from the learning information used at the time of the generation of the inference model and test image information based on this test image (image information on which the labeling processing is performed using the test image) are prepared, and inference processing using the generated inference model is performed on this test image and an accuracy is calculated by comparing a result of this inference and the test image information, as another method.

In the inference model confirmation process S211 according to the present embodiment, for example, at least one of the above-described one method and other method is performed. Then, if any one of them is performed, the accuracy at this time is stored into a predetermined memory. If both of them are performed, the accuracy of each of them is stored into the predetermined memory.

Next, in the present embodiment, whether the result of the inference model confirmation process S211 is an expected value or higher is determined (an inference model determination process: step S213). At this time, whether the result of the inference model confirmation process S211 is the expected value or higher is determined by comparing the accuracy in the inference model confirmation process S211 that is stored in the memory and the expected value. Examples of the expected value include an accuracy of 95% or higher in the case of the comparison with the learning information and an accuracy of 90% or higher in the case of the comparison with the test image information.

In the inference model determination process S213, if the accuracy of the generated inference model is determined to be equal to or higher than the predetermined expected value (if "YES" is determined in S213), the construction of the inference model is ended. If the accuracy of the generated inference model is determined not to be equal to or higher than the predetermined expected value (if "NO" is determined in S213), the processing in and after step S209 is repeatedly performed via processing in step S215 (an adjustment process).

If the processing in and after step S209 is performed again after the processing in step S213, the adjustment process S215 for appropriately generating the inference model is performed as described above.

Examples of the adjustment process S215 according to the present embodiment include, for example, a method of changing a learning rate, a batch size, and/or a dropout rate, which are parameters used in the learning. Further, in the adjustment process S215, the learning information and the test image information may be shuffled or each piece of information may be increased or reduced as necessary. Further, in the present embodiment, a further appropriate inference model may be constructed by generating a plurality of models as necessary and performing the inference model determination process S213, the adjustment process S215, and the like with respect to each of them.

The present embodiment has been described referring to the configuration in which the processing in and after step S215 is performed if the accuracy of the generated inference model is determined not to be equal to or higher than the predetermined expected value (if "NO" is determined in S213), but the present invention is not limited thereto. Therefore, for example, the present embodiment may be configured to perform the processing in and after step S201 again if the accuracy is determined not to be equal to or higher than the predetermined expected value. More specifically, for example, the present embodiment may be configured to return to the processing in step S201 and perform the processing in and after the image acquisition process S201 if a result equal to or higher than the intended expected value cannot be acquired even when the adjustment process S215 is repeated a plurality of times (three times or the like).

In the present embodiment, the determination that the generated inference model is equal to or higher than the expected value in the inference model determination process S213 (the determination of "Yes" in S213) leads to the completion of the "inference model" according to the present embodiment.

In the present embodiment, the processing for discriminating the sorting target S is performed using the inference model generated in the above-described manner. More specifically, the inference model is installed in, for example, the controller (not illustrated) electrically connected to the X-ray discriminator 10 illustrated in FIG. 1, and the processing for discriminating the sorting target S is performed using this inference model.

In the following description, the method for discriminating the sorting target S according to the present embodiment will be described with reference to FIGS. 1, 4, 5A to 5C, and the like. FIG. 4 illustrates a flowchart regarding the method for discriminating the sorting target performed using the X-ray discriminator 10 according to the present embodiment. Further, FIGS. 5A to 5C illustrate schematic views of the imaging information and the like in the discrimination method (at the time of a discrimination process) performed using the X-ray discriminator 10 according to the present embodiment. FIG. 5A illustrates the raw image captured by irradiating the sorting target with the X-ray. FIG. 5B illustrates the inference result image acquired when the inference model is applied to the captured raw image. FIG. 5C illustrates the post-filter processing image acquired when the inference result image is filtered.

As illustrated in FIGS. 1 and 4, in the discrimination method according to the present embodiment, the imaging processing regarding the sorting target S during the transfer process is performed using the X-ray generation portion 11 and the X-ray detection portion 12 (one non-limiting example of "imaging" in the claims: step S401). In the present embodiment, in the step S401 (the imaging process), a line-shaped raw image 510 is acquired regarding the plurality of sorting targets S on the conveyance path 91 (refer to FIG. 5A). More specifically, in step S401, sorting targets SS are irradiated with the X-ray from the X-ray generation portion 11. Image information corresponding to the predetermined number of lines (for example, 512 lines) is captured by the X-ray detection portion 12. This image information (the raw image 510) is appropriately stored into the memory. Further, in the present embodiment, the normalization processing is appropriately performed on the raw image 510.

Next, in the present embodiment, an inference model execution process S403 is performed with the image acquired in the imaging process (the raw image 510 after the normalization processing) handled as input data (one non-limiting example of "imaging information" in the claims). In other words, the inference model is applied to the raw image 510 captured in the imaging process S401 (the raw image after the normalization processing) (step S403), and a result of this inference (an inference result image 520) can be acquired (step S405).

FIG. 5B illustrates the inference result image 520 when the inference model is applied to the captured raw image 510. As illustrated in FIG. 5B, the application of the inference model results in assignment of one label selected from an acceptable portion labeling portion SSP1 (the classification information), a defective portion labeling portion SSP2 (the classification information), an adjacency labeling portion SSP3 (the adjacency information), and a background labeling portion SSP4 (the background information) (one label of the four labels) to all of the pixels in the inference result image 520.

Next, in the present embodiment, a filtering processing process (step S407) is performed on the inference result image 520 acquired in the inference model execution process S403.

Examples of the filtering processing include a method of confirming how many pixels labeled as a defective portion (the defective portion labeling portion SSP2) are contained in a predetermined image size, and handling this region as a defective portion if the number of pixels is larger than a predetermined value and handling this region as an acceptable portion if the number of pixels is smaller than the predetermined value. Other examples of the filtering processing include processing such as smoothing, edge extraction, sharpening, and morphological transformation.

As a result of the execution of the filtering processing S407, for example, the defective portion labeling portion SSP2 in the inference result image 520 is reduced in size (for example, reduced in size by 20% to 50%), and the defective portion labeling portion SSP2 and the adjacency labeling portion SSP3 having the number of pixels equal to or smaller than the predetermined value are deleted and replaced with another labeling portion.

More specifically, as a result of the filtering processing S407, the defective portion labeling portion SSP2 in the inference result image 520 is displayed in a smaller size by way of example. Alternatively, as another example of the result of the filtering processing S407, the image is displayed while the defective portion labeling portion SSP2 having the number of pixels equal to or smaller than the predetermined value in the inference result image 520 is replaced with the acceptable portion labeling portion (an "acceptable portion" at the time of the classification identification, which will be described below) or the background labeling portion (a "background portion" at the time of the classification identification, which will be described below). Further, the image is displayed with the adjacency labeling portion SSP3 replaced with the background portion (the "background portion" at the time of the classification identification, which will be described below). The image after being subjected to the filtering processing S407 is a post-filter processing image 530 (refer to FIG. 5C).

In the present embodiment, the filtering processing S407 is performed on the inference result image 520 (refer to FIG. 5B) acquired in the inference result S405 as described above. Then, the post-filter processing image 530 illustrated in FIG. 5C is formed by performing this filtering processing S407, and processing for identifying the classification (discrimination processing or the discrimination process based on the identification of the classification) is performed based on this post-filter processing image 530 (step S409).

As illustrated in FIGS. 5B and 5C, two defective portion labeling portions SSP2 (FIG. 5B) in the inference result image 520 are reduced in size by approximately 30% and defective portions C2 (FIG. 5C) are identified as a result of the filtering in the post-filter processing image 530 acquired by performing the filtering processing process S407 on the inference result image 520. Further, the adjacency labeling portion SSP3 (FIG. 5B) in the inference result image 520 is identified as a background portion C4 (FIG. 5C) as a result of the filtering. Further, the acceptable portion labeling portions SSP1 and the background labeling portion SSP4 in FIG. 5B are identified as acceptable portions C1 and a background portion C4 in FIG. 5C as a result of the filtering.

In other words, in the present embodiment, the "acceptable portion," the "defective portion," and the "background portion" are identified based on the post-filter processing image 530. In the present embodiment, the adjacency labeling portion where sorting targets are located adjacent to each other is identified as the "background portion".

In the present embodiment, various kinds of information are assigned pixel by pixel, which means that, for example, the inference result image 520 is subjected to the assignment of one label selected from the acceptable portion labeling portion SSP1 (the classification information), the defective portion labeling portion SSP2 (the classification information), the adjacency labeling portion SSP3 (the adjacency information), and the background labeling portion SSP4 (the background information) (one label of the four labels) to each of the pixels therein. Then, in the present embodiment, the processing for identifying the classification (the discrimination processing or the discrimination process) S409 is performed with respect to each of the pixels in the post-filter processing image 530 acquired by performing the filtering processing S407 on the inference result image 520, and each of the pixels is identified as one of the "acceptable portion", the "defective portion", and the "background portion".

In the present embodiment, the background portion C4 and a plurality of sorting targets are identified as a result of the classification identification processing S409 as illustrated in FIG. 5C, and, more specifically, two individuals having the defective portion C2 (sorting targets CA and CB) are identified (discriminated), and the other sorting targets are identified (discriminated) as individuals (sorting targets) having only the acceptable portion C1.

Next, in the present embodiment, whether to end the processing for discriminating the sorting target is determined after the classification identification processing S409 (step S411). At this time, if it is determined to end the discrimination processing (if "YES" is determined in S411), the discrimination processing using the X-ray discriminator 10 (the process of discriminating the sorting target) is ended. If it is determined not to end the discrimination processing (if "NO" is determined in S411), the processing in and after step S401 is repeatedly performed.

More specifically, if there is the sorting target S conveyed on the conveyance path 91 and the imaging process is ongoing using the X-ray generation portion 11, the X-ray detection portion 12, and the like, the discrimination processing is continuously performed unless otherwise especially instructed.

The present embodiment is configured to discriminate the sorting target S by performing the imaging processing process, the inference model execution process (the inference result), the filtering processing process, the classification identification process, and the like using the X-ray discriminator 10, the inference model, and the like, as described above.

The discrimination apparatus (the discriminator) forming the apparatus for sorting the sorting target according to the present embodiment is configured and functions in the manner described with reference to FIGS. 1 to 5C, thereby bringing about the following advantageous effects. In the following description, the configuration and the advantageous effects of the discrimination method performed using the discrimination apparatus according to the present embodiment will be described.

The method for discriminating the sorting target according to the present embodiment includes the transfer process of transferring the sorting target, the imaging process of imaging the sorting target during the transfer process, and the discrimination process of discriminating the sorting target based on the imaging information (the raw image 510) acquired in the imaging process. The discrimination process is performed using the inference model generated based on the learning information regarding the sorting target (the labeling image group 330 or the labeling images 331 to 336). The learning information (the labeling image group 330 or the labeling images 331 to 336) includes the adjacency information between sorting targets (the adjacency labeling portion SP3) and the classification information of the sorting target (the acceptable portion labeling portion SP1 and the defective portion labeling portion SP2). The discrimination process includes discriminating the sorting target using the imaging information and the inference model.

The method for discriminating the sorting target according to the present embodiment is configured in this manner, and therefore can acquire the following advantageous effects.

The discrimination method according to the present embodiment makes it easy to compare the inference result and the imaging information, and therefore can enhance the efficiency of the calculation processing at the time of the discrimination. Further, the discrimination method according to the present embodiment uses the adjacency information (the adjacency labeling portion SP3), and therefore can prevent the adjacency portion from being falsely recognized as the defective portion, thereby improving the discrimination accuracy. Further, the discrimination method according to the present embodiment allows sorting targets in a contact state to be recognized as a separated state by using the adjacency information, thereby allowing each sorting target to be further accurately discriminated. Further, the discrimination method according to the present embodiment does not require processing for cutting out an object as illustrated in FIGS. 5A to 5C, and therefore can increase the processing speed of the discrimination processing. Further, according to the present embodiment, the defective portion can be easily identified by converting the inference result into the image. Further, according to the present embodiment, the result is output pixel by pixel, and this means that each piece of pixel data can be easily used for various kinds of processing (post-processing and the like). Further, according to the present embodiment, handling the inference result as the image makes it possible to apply an image processing technique.

Alternatively, the method for discriminating the sorting target according to the present embodiment may be configured in the following manner. The method includes the transfer process of transferring the sorting target, the imaging process of imaging the sorting target during the transfer process, and the discrimination process of discriminating the sorting target based on the imaging information (the raw image 510) acquired in the imaging process. The discrimination process is performed using the inference model generated based on the learning information regarding the sorting target (the labeling image group 330 or the labeling images 331 to 336). The learning information (the labeling image group 330 or the labeling images 331 to 336) includes the adjacency information between sorting targets (the adjacency labeling portion SP3), the classification information of the sorting target (the acceptable portion labeling portion SP1 and the defective portion labeling portion SP2), and the background information of the sorting target (the background labeling portion SP4). The discrimination process includes discriminating the sorting target using the imaging information and the inference model.

According to such a configuration, the following advantageous effects can be acquired in addition to the above-described various advantageous effects.

The discrimination method according to the present embodiment allows each sorting target to be clearly discriminated since the learning information includes the background information of the sorting target. Further, the discrimination method according to the present embodiment identifies the adjacency information (the adjacency labeling portion SP3) and thereafter converts this adjacency information into the background information, and therefore achieves processing for further clearly discriminating each sorting target.

In the present embodiment, as illustrated in FIGS. 1 to 5C, the "inference model" is generated, and the "inference model" generated in this manner is installed in the discrimination apparatus (the discriminator) forming the sorting apparatus and the discrimination method is performed using them.

In the following description, the sorting apparatus including the discrimination apparatus with the above-described inference model installed therein will be described with reference to the drawings and the like.

Figure 6:
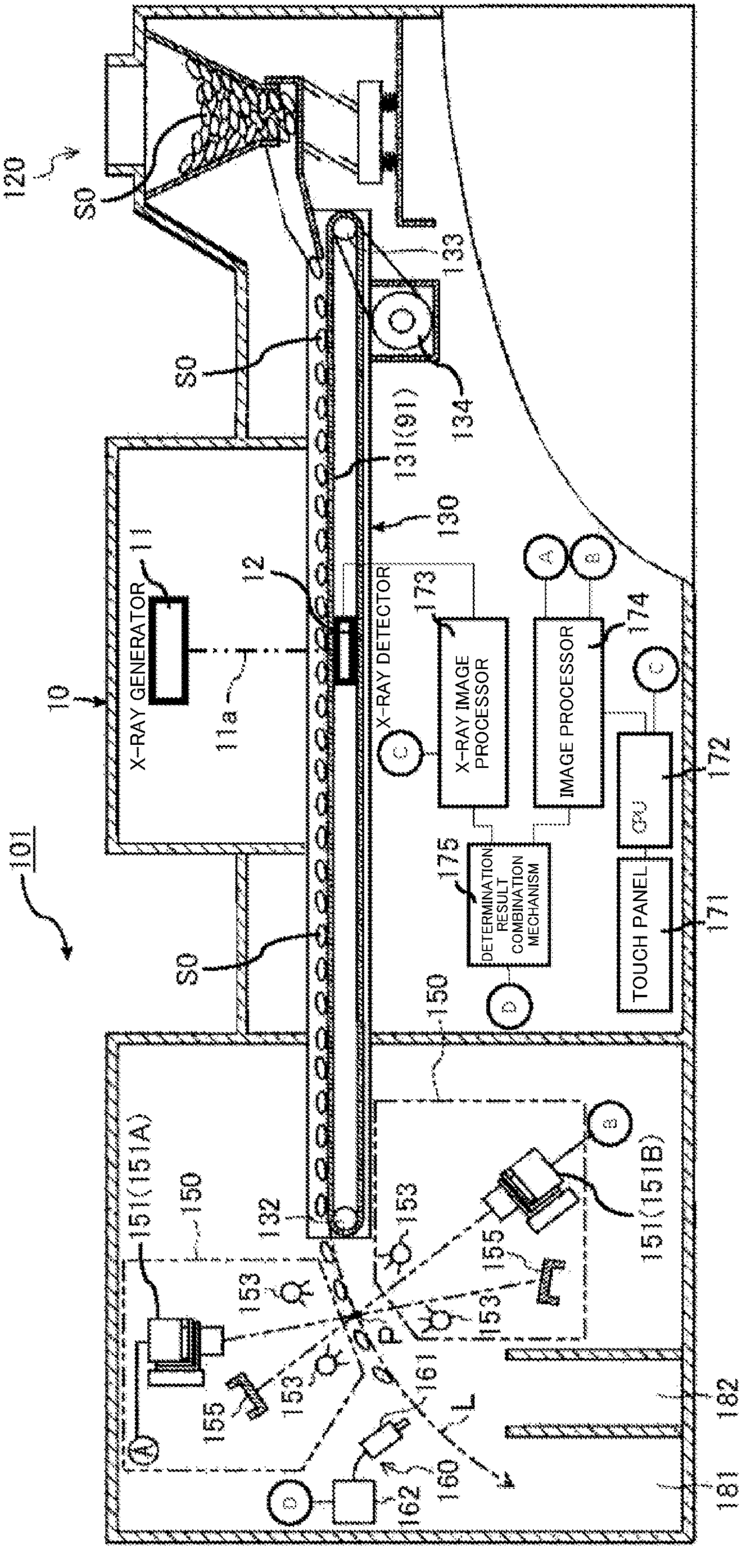
FIG. 6 illustrates a schematic configuration diagram of a sorting apparatus (a belt-type sorting apparatus) according to a second embodiment of the present disclosure.

<Second Embodiment> FIG. 6 illustrates a schematic configuration diagram of a sorting apparatus (a belt-type sorting apparatus) according to a second embodiment of the present disclosure. More specifically, this FIG. 6 illustrates a schematic configuration diagram of a belt-type sorting apparatus 101 equipped with the discrimination apparatus (the discriminator) described with reference to FIGS. 1 to 5C.

As illustrated in FIG. 6, the sorting apparatus 101 according to the present embodiment includes a sorting target feeding portion 120, which feeds a sorting target S0, a conveyance portion 130, which conveys the sorting target S0, an optical detection portion 150, which optically detects the sorting target S0, a sorting portion 160, which performs processing for sorting the sorting target S0, the X-ray discrimination apparatus 10, and the like.

In the sorting apparatus 101 according to the present embodiment, the sorting target S0 stored in the sorting target feeding portion 120 is fed to one end portion of the conveyance portion 130, and the imaging processing (the discrimination processing based thereon) is performed on the fed sorting target S0 by the X-ray discrimination apparatus 10 during the conveyance by the conveyance portion 130 (during the transfer process). Next, the sorting target S0 conveyed by the conveyance portion 130 is ejected so as to fall along a falling trajectory L from the other end portion of the conveyance portion 130, and the optical detection portion 150 and the sorting portion 160 are provided around the ejected sorting target S0. The sorting apparatus 101 according to the present embodiment is configured to drive the sorting portion 160 based on a discrimination signal acquired from at least one of the X-ray discrimination apparatus 10 and the optical detection portion 150, and the sorting target S0 is subjected to the sorting processing by the sorting portion 160 to be sorted into either an acceptable product containing portion 181 or a defective product discharge portion 182.

The sorting target feeding portion 120 forming the sorting apparatus 101 according to the present embodiment includes a storage portion storing the sorting target S0, a vibration feeder, and the like. The sorting target feeding portion 120 is configured to feed the sorting target S0 from the sorting target feeding portion 120 to the one end portion of the conveyance portion 130 as necessary.

The conveyance portion 130 forming the sorting apparatus 101 according to the present embodiment includes a conveyance belt 131, conveyance rollers 132 and 133, a driving motor 134, and the like. The conveyance belt 131 is endlessly wound between the rollers 132 and 133 provided in parallel with each other. The driving motor 134 is coupled with the roller 133, which is one of the rollers, via a belt or the like. The conveyance belt 131 is configured to be rotationally driven at a constant speed by rotating the driving motor 134. The conveyance belt 131 forming the conveyance portion 130 corresponds to the conveyance path 91 in the first embodiment.

The X-ray discrimination apparatus 10 described in the first embodiment is provided at an approximately central portion in a conveyance direction of the conveyance portion 130 according to the present embodiment. More specifically, as illustrated in FIG. 6, the X-ray generation portion 11 is provided at a position above the sorting target S0 on the conveyance belt 131 (the conveyance path 91 in the first embodiment), and the X-ray detection portion 12 is provided at a position below the sorting target S0 (inside the conveyance belt 131 in FIG. 6). The imaging information acquired by the X-ray discrimination apparatus 10 is transmitted to an X-ray image processor 173, which will be described below. Further, in the present embodiment, a partition wall is appropriately provided to prevent a leak of the X-ray.

The optical detection portion 150 forming the sorting apparatus 101 according to the present embodiment is provided near the falling trajectory L taken when the sorting target S0 fed from the sorting target feeding portion 120 to the one end portion of the conveyance portion 130 (the conveyance belt 131 included therein) is ejected from the other end portion of the conveyance portion 130 (the conveyance belt 131). More specifically, the optical detection portion 150 includes a light-receiving portion 151 (a first light-receiving portion 151A and a second light-receiving portion 151B), a plurality of light-emitting portions 153, background portions 155 respectively corresponding to the light-receiving portions 151A and 151B, and the like. In the present embodiment, as illustrated in FIG. 6, the two light-receiving portions 151A and 151B are provided at positions generally symmetric with respect to the falling trajectory L. The light-receiving portion 151 includes a solid-state image sensor (a CCD image sensor, a CMOS image sensor, or the like), and the like. The light-emitting portions 153 are configured to irradiate an optical detection position P on the falling trajectory L with light having a predetermined wavelength from a plurality of angles. The light-receiving portion 151 images the sorting target S0 that reaches the optical detection position P on the falling trajectory L, and the imaging information (a light-receiving signal) regarding each sorting target S0 is transmitted to the image processor 174, which will be described below.

The sorting portion 160 forming the sorting apparatus 101 according to the present embodiment includes a nozzle portion 161, an electromagnetic valve 162, and the like. The nozzle portion 161 is configured to eject fluid (for example, air) toward the sorting target S0 on the falling trajectory L. The electromagnetic valve 162 is provided between a fluid supply portion (for example, an air compressor, which is not illustrated) and the nozzle portion 161, and is configured to control the fluid supply to the nozzle portion 161 based on a signal from a determination result combination mechanism 175, which will be described below.

Further, as illustrated in FIG. 6, the sorting apparatus 101 according to the present embodiment includes a touch panel 171, which can receive inputs of various signals and the like when the apparatus is in use, and the touch panel 171 is electrically connected to a CPU 172 of the sorting apparatus 101. Further, the CPU 172 is electrically connected to the X-ray image processor 173 and the image processor 174. Further, the X-ray image processor 173 and the image processor 174 are electrically connected to the determination result combination mechanism 175.

The X-ray image processor 173 is configured in such a manner that the imaging information from the X-ray detector 11 can be transmitted thereto, and the image processor 174 is configured in such a manner that the imaging information from the two light-receiving portions 151A and 151B can be transmitted thereto. Further, the determination result combination mechanism 175 and the electromagnetic valve 162 are electrically connected to each other, and ejection mode (an ejection duration, an ejection timing, and the like) of the fluid ejected from the nozzle portion 161 is controlled via the electromagnetic valve 162 based on a discrimination signal from the determination result combination mechanism 175.

The sorting apparatus 101 according to the present embodiment is configured in this manner, and functions in the following manner.

In the present embodiment, the sorting target S0 fed from the sorting target feeding portion 120 is conveyed (transferred) by the conveyance portion 130, and the imaging processing (the imaging process) is performed on the sorting target S0 during the conveyance (during the transfer process) by the X-ray discrimination apparatus 10. Next, in the present embodiment, the imaging processing (the imaging process) is performed on the sorting target S0 ejected from the conveyance portion 130 by the optical detection portion 150. Next, in the present embodiment, the sorting processing (the sorting process) using the sorting portion 160 is performed based on the discrimination signal derived from at least one of the imaging information of the X-ray discrimination apparatus 10 and the imaging information of the X-ray detection portion 150. In other words, the ejection timing, the ejection duration, and the like of the fluid ejected from the nozzle portion 161 are controlled via the electromagnetic valve 162 based on the discrimination signal, and the sorting target S0 is sorted by the fluid ejected from the nozzle portion 161 into either the acceptable product containing portion 181 or the defective product discharge portion 182.

When the sorting apparatus 101 according to the present embodiment is in use, first, actuation condition information such as various kinds of information regarding the sorting target S0 and sorting conditions (discrimination conditions) is input to the CPU 172 of the apparatus with use of the touch panel 171 from which a predetermined signal can be output. This actuation condition information is transmitted to the X-ray image processor 173 and the image processor 174 via the CPU 172. According to the contents of this actuation condition information, for example, the X-ray image processor 173 selects one inference model from a plurality of inference models and sets a predetermined threshold value. Further, the image processor 174, for example, also sets a predetermined threshold value. The present embodiment is configured in such a manner that the plurality of inference models, a plurality of threshold values (a plurality of threshold values used in the discrimination), and the like can be implemented on the CPU 172 (or at least one of the X-ray image processor 173 and the image processor 174).

In the present embodiment, after the actuation condition information is input using the touch panel 171, the sorting apparatus 101 is driven, and the imaging information from the X-ray detector 12 regarding the sorting target S0 is transmitted to the X-ray image processor 173 and the imaging information from the light-receiving portions 151A and 151B regarding the sorting target S0 is transmitted to the image processor 174. The imaging information transmitted to the X-ray image processor 173 and the image processor 174 is transmitted to the determination result combination mechanism 175 via predetermined proper calculation processing (or directly as this imaging information itself). The determination result combination mechanism 175 performs calculation processing based on the imaging information from the X-ray image detector 173 and the imaging information from the image processor 174 with respect to the same sorting target S0 in consideration of the conveyance speed of the sorting target S0 and the like, and transmits the discrimination signal (an electromagnetic valve control signal) based on a combined determination result therefrom to the electromagnetic valve 162. The ejection mode of the fluid ejected from the nozzle portion 161 is controlled via this electromagnetic valve 162, and the processing for sorting the sorting target S0 is performed with the aid of this ejected fluid.

The present embodiment is configured in such a manner that, as described above, the sorting apparatus 101 is formed using the X-ray discrimination apparatus 10 (the X-ray discriminator), the inference model, and the like described in the first embodiment, and the sorting apparatus 101 performs the imaging processing process, the inference model execution process (the inference result), the filtering processing process, the classification identification process, and the like, thereby discriminating and sorting the sorting target S0 (the discrimination processing and the sorting processing).

The sorting apparatus 101 according to the present embodiment is configured and functions in the manner described with reference to FIG. 6 and the like (FIGS. 1 to 5C for the X-ray discrimination apparatus 10), thereby bringing about the following advantageous effects. In the following description, the configuration and the advantageous effects of the sorting apparatus (the sorting method) according to the present embodiment will be described.

The sorting method according to the present embodiment includes the transfer process of transferring the sorting target S0, the imaging process of imaging the sorting target S0 during the transfer process, the discrimination process of discriminating the sorting target S0 based on the imaging information acquired in the imaging process, and the sorting process of sorting the sorting target S0 based on the discrimination information acquired in the discrimination process. The discrimination process is performed using the inference model generated based on the learning information regarding the sorting target S0. The learning information includes the adjacency information between sorting targets and the classification information of the sorting target. The discrimination process includes discriminating the sorting target S0 using the imaging information and the inference model.

Further, the sorting apparatus according to the present embodiment includes the conveyance portion 130 (the transfer portion) configured to transfer the sorting target S0, the X-ray discrimination apparatus 10 (the imaging portion) configured to image the sorting target S0 during the transfer by the conveyance portion 130, the discriminator (the discrimination portion formed by at least one of the X-ray image processor 173 and the determination result combination mechanism 175) configured to discriminate the sorting target S0 based on the imaging information acquired by the X-ray discrimination apparatus 10, and the sorting portion 160 (the sorting portion) configured to sort the sorting target S0 based on the discrimination signal (the discrimination information) acquired by the discriminator. The discriminator includes the inference model generated based on the learning information regarding the sorting target. The learning information includes the adjacency information between sorting targets and the classification information of the sorting target. The discriminator discriminates the sorting target S0 using the imaging information and the inference model.

The sorting apparatus (the sorting method) according to the present embodiment is configured in this manner, and therefore can acquire the following advantageous effects.

The sorting apparatus (the sorting method) according to the present embodiment makes it possible to easily compare the inference result and the imaging information to thus enhance the efficiency of the calculation processing when the discrimination signal is generated by the discriminator, and the sorting portion is controlled based on the discrimination signal acquired in this manner. Therefore, the sorting apparatus according to the present embodiment can promote the efficiency of the calculation processing when sorting the sorting target S0.

Further, the sorting apparatus (the sorting method) according to the present embodiment uses the adjacency information (the adjacency labeling portion SP3) when generating the discrimination signal, and therefore can prevent the adjacency portion from being falsely recognized as the defective portion, thereby improving the discrimination accuracy of the discrimination signal. Therefore, the sorting apparatus according to the present embodiment can achieve highly accurate sorting processing using this discrimination signal having high discrimination accuracy.

Further, the sorting apparatus (the sorting method) according to the present embodiment allows sorting targets in a contact state to be recognized as a separated state by using the adjacency information, thereby allowing each sorting target to be further accurately discriminated and sorted.

Further, the sorting apparatus (the sorting method) according to the present embodiment does not require processing for cutting out an object when discriminating the sorting target S0 as illustrated in above-described FIGS. 5A to 5C, and therefore can increase the processing speed of the discrimination processing and thus can increase the speed of the sorting processing.

Further, the sorting apparatus according to the present embodiment includes the conveyance portion 130 (the transfer portion) configured to transfer the sorting target S0, the X-ray discrimination apparatus 10 (the imaging portion) configured to image the sorting target S0 during the transfer by the conveyance portion 130, the discriminator (the discrimination portion formed by at least one of the X-ray image processor 173 and the determination result combination mechanism 175) configured to discriminate the sorting target S0 based on the imaging information acquired by the X-ray discrimination apparatus 10, and the sorting portion 160 (the sorting portion) configured to sort the sorting target S0 based on the discrimination signal (the discrimination information) acquired by the discriminator. The discriminator includes the inference model generated based on the learning information regarding the sorting target. The learning information includes the adjacency information between sorting targets, the classification information of the sorting target, and the background information of the sorting target. The discriminator discriminates the sorting target S0 using the imaging information and the inference model.

According to such a configuration, the following advantageous effects can be acquired in addition to the above-described various advantageous effects.

The sorting apparatus according to the present embodiment can clearly discriminate each sorting target when generating the discrimination signal to thus acquire a highly accurate discrimination signal, since the learning information includes the background information of the sorting target. Therefore, the sorting apparatus according to the present embodiment can realize highly accurate sorting processing using this highly accurate discrimination signal.

Further, the sorting apparatus according to the present embodiment identifies the adjacency information and thereafter converts this adjacency information into the background information, and therefore can achieve processing for further clearly discriminating each sorting target and acquire a highly accurate discrimination signal. Therefore, the sorting apparatus according to the present embodiment can realize highly accurate sorting processing.

Figure 7:
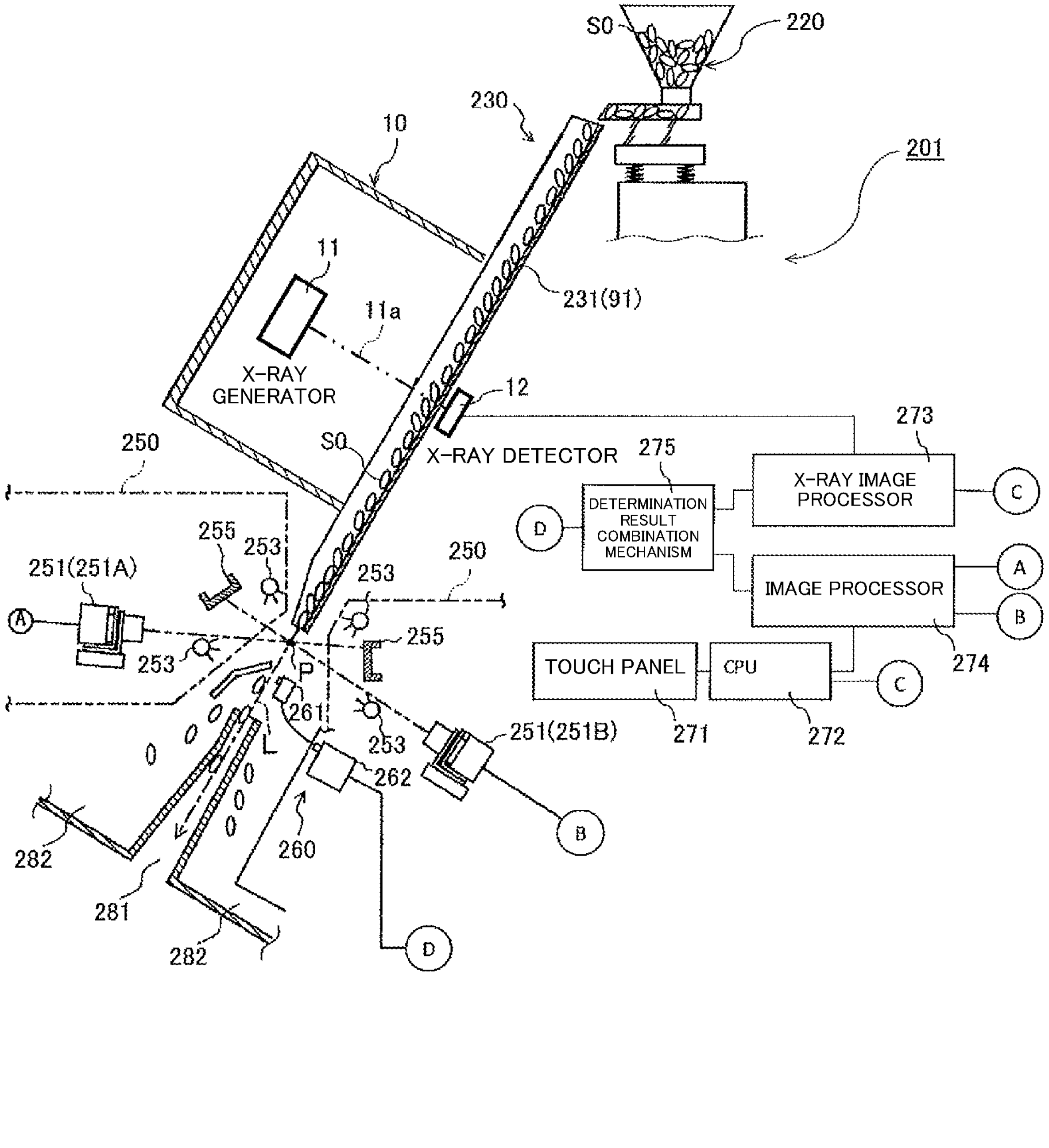
FIG. 7 illustrates a schematic configuration diagram of a sorting apparatus (a chute-type sorting apparatus) according to a third embodiment of the present disclosure.

<Third Embodiment> FIG. 7 illustrates a schematic configuration diagram of a sorting apparatus (a chute-type sorting apparatus) according to a third embodiment of the present disclosure. More specifically, this FIG. 7 illustrates a schematic configuration diagram of a chute-type sorting apparatus 201 equipped with the discrimination apparatus (the discriminator) described with reference to FIGS. 1 to 5C.

As illustrated in FIG. 7, the sorting apparatus 201 according to the present embodiment includes a sorting target feeding portion 220, which feeds the sorting target S0, a chute 230 (the conveyance portion or the transfer portion), which transfers the sorting target S0, an optical detection portion 250, which optically detects the sorting target S0, a sorting portion 260, which performs processing for sorting the sorting target S0, the X-ray discrimination apparatus 10, and the like.

In the sorting apparatus 201 according to the present embodiment, the sorting target S0 stored in the sorting target feeding portion 220 is fed to one end portion of an inclined plate portion 231 forming the chute 230, and the imaging processing (the discrimination processing based thereon) is performed by the X-ray discrimination apparatus 10 on the sorting target S0 that is fed and is gravitationally falling (flowing down) on the inclined plate portion 231 (during the transfer process). Next, the sorting target S0 falling on the chute 230 is ejected so as to fall along the falling trajectory L from the other end portion of the inclined plate portion 231, and the optical detection portion 250 and the sorting portion 260 are provided around the ejected sorting target S0. The sorting apparatus 201 according to the present embodiment is configured to drive the sorting portion 260 based on a discrimination signal acquired from at least one of the X-ray discrimination apparatus 10 and the optical detection portion 250, and the sorting target S0 is subjected to the sorting processing by the sorting portion 260 to be sorted into either an acceptable product containing portion 281 or a defective product discharge portion 282.

The sorting target feeding portion 220 forming the sorting apparatus 201 according to the present embodiment includes a storage portion storing the sorting target S0, a vibration feeder, and the like. The sorting target feeding portion 220 is configured to feed the sorting target S0 from the sorting target feeding portion 220 to the one end portion of the inclined plate portion 231 forming the chute 230 as necessary.

The chute 230 forming the sorting apparatus 101 according to the present embodiment includes the inclined plate portion 231. The inclined plate portion 231 is arranged so as to be inclined at, for example, approximately 30° to 70° with respect to a ground contact surface (a horizontal surface) in consideration of the installation region in the apparatus, the falling speed (the downward flowing speed) of the gravitationally falling sorting target S0, and the like. Further, the inclination angle of the inclined plate portion 231 may be set to an angle larger than the angle of repose of the sorting target and not causing the sorting target flowing down on the inclined plate portion 231 to bounce up. In the present embodiment, the inclined plate portion 231 forming the chute 230 is configured to be inclined at approximately 60 degrees with respect to the ground contact surface. The inclined plate portion 231 forming the chute 230 corresponds to the conveyance path 91 in the first embodiment.

The X-ray discrimination apparatus 10 described in the first embodiment is provided at an approximately central portion of the chute 230 according to the present embodiment. More specifically, as illustrated in FIG. 7, the X-ray generation portion 11 is provided at a position above the sorting target S0 gravitationally falling on the inclined plate portion 231 (the conveyance path 91 in the first embodiment), and the X-ray detection portion 12 is provided at a position below the sorting target S0 (a position below the inclined plate portion 231 in FIG. 7). The imaging information acquired by the X-ray discrimination apparatus 10 is transmitted to an X-ray image processor 273, which will be described below. Further, in the present embodiment, a partition wall is appropriately provided to prevent a leak of the X-ray.

The optical detection portion 250 forming the sorting apparatus 201 according to the present embodiment is provided near the falling trajectory L taken when the sorting target S0 fed from the sorting target feeding portion 220 to the one end portion of the chute 230 (the inclined plate portion 231 included therein) is ejected from the other end portion of the chute 230 (the inclined plate portion 231). More specifically, the optical detection portion 250 includes a light-receiving portion 251 (a first light-receiving portion 251A and a second light-receiving portion 251B), a plurality of light-emitting portions 253, background portions 255 respectively corresponding to the light-receiving portions 251A and 251B, and the like. In the present embodiment, as illustrated in FIG. 7, the two light-receiving portions 251A and 251B are provided at positions generally symmetric with respect to the falling trajectory L. The light-receiving portion 251 includes a solid-state image sensor (a CCD image sensor, a CMOS image sensor, or the like), and the like. The light-emitting portions 253 are configured to irradiate the optical detection position P on the falling trajectory L with light having a predetermined wavelength from a plurality of angles. The light-receiving portion 251 images the sorting target S0 that reaches the optical detection position P on the falling trajectory L, and the imaging information (a light-receiving signal) regarding each sorting target S0 is transmitted to the image processor 274, which will be described below.

The sorting portion 260 forming the sorting apparatus 201 according to the present embodiment includes a nozzle portion 261, an electromagnetic valve 262, and the like. The nozzle portion 261 is configured to eject fluid (for example, air) toward the sorting target S0 on the falling trajectory L. The electromagnetic valve 262 is provided between a fluid supply portion (for example, an air compressor, which is not illustrated) and the nozzle portion 261, and is configured to control the fluid supply to the nozzle portion 261 based on a signal from a determination result combination mechanism 275, which will be described below.

Further, as illustrated in FIG. 7, the sorting apparatus 201 according to the present embodiment includes a touch panel 271, which can receive inputs of various signals and the like when the apparatus is in use, and the touch panel 271 is electrically connected to a CPU 272 of the sorting apparatus 201. Further, the CPU 272 is electrically connected to the X-ray image processor 273 and the image processor 274. Further, the X-ray image processor 273 and the image processor 274 are electrically connected to the determination result combination mechanism 275.

The X-ray image processor 273 is configured in such a manner that the imaging information from the X-ray detector 11 can be transmitted thereto, and the image processor 274 is configured in such a manner that the imaging information from the two light-receiving portions 251A and 251B can be transmitted thereto. Further, the determination result combination mechanism 275 and the electromagnetic valve 262 are electrically connected to each other, and ejection mode (an ejection duration, an ejection timing, and the like) of the fluid ejected from the nozzle portion 261 is controlled via the electromagnetic valve 262 based on a discrimination signal from the determination result combination mechanism 275.

The sorting apparatus 201 according to the present embodiment is configured in this manner, and functions in the following manner.

In the present embodiment, the sorting target S0 fed from the sorting target feeding portion 220 is conveyed (transferred) by the chute 230, and the imaging processing (the imaging process) is performed on the sorting target S0 during the conveyance (during the transfer process) by the X-ray discrimination apparatus 10. Next, in the present embodiment, the imaging processing (the imaging process) is performed on the sorting target S0 ejected from the conveyance portion 230 by the optical detection portion 250. Next, in the present embodiment, the sorting processing (the sorting process) using the sorting portion 260 is performed based on the discrimination signal derived from at least one of the imaging information of the X-ray discrimination apparatus 10 and the imaging information of the optical detection portion 250. In other words, the ejection timing, the ejection duration, and the like of the fluid ejected from the nozzle portion 261 are controlled via the electromagnetic valve 262 based on the discrimination signal, and the sorting target S0 is sorted into either the acceptable product containing portion 281 or the defective product discharge portion 282 with the aid of the fluid ejected from the nozzle portion 261.

When the sorting apparatus 201 according to the present embodiment is in use, first, actuation condition information such as various kinds of information regarding the sorting target S0 and sorting conditions (discrimination conditions) is input to the CPU 272 of the apparatus with use of the touch panel 271 from which a predetermined signal can be output. This actuation condition information is transmitted to the X-ray image processor 273 and the image processor 274 via the CPU 272. According to the contents of this actuation condition information, for example, the X-ray image processor 273 selects one inference model from a plurality of inference models and sets a predetermined threshold value. Further, the image processor 274, for example, also sets a predetermined threshold value. The present embodiment is configured in such a manner that the plurality of inference models, a plurality of threshold values (a plurality of threshold values used in the discrimination), and the like can be implemented on the CPU 272 (or at least one of the X-ray image processor 273 and the image processor 274).

In the present embodiment, after the actuation condition information is input using the touch panel 271, the sorting apparatus 201 is driven, and the imaging information from the X-ray detector 12 regarding the sorting target S0 is transmitted to the X-ray image processor 273 and the imaging information from the light-receiving portions 251A and 251B regarding the sorting target S0 is transmitted to the image processor 274. The imaging information transmitted to the X-ray image processor 273 and the image processor 274 is transmitted to the determination result combination mechanism 275 via predetermined proper calculation processing (or directly as this imaging information itself). The determination result combination mechanism 275 performs calculation processing based on the imaging information from the X-ray image detector 273 and the imaging information from the image processor 274 with respect to the same sorting target S0 in consideration of the conveyance speed of the sorting target S0 and the like, and transmits the discrimination signal (an electromagnetic valve control signal) based on a combined determination result therefrom to the electromagnetic valve 262. The ejection mode of the fluid ejected from the nozzle portion 261 is controlled via the electromagnetic valve 262, and the processing for sorting the sorting target S0 is performed with the aid of this ejected fluid.

The present embodiment is configured in such a manner that, as described above, the sorting apparatus 201 is formed using the X-ray discrimination apparatus 10 (the X-ray discriminator), the inference model, and the like described in the first embodiment, and the sorting apparatus 201 performs the imaging processing process, the inference model execution process (the inference result), the filtering processing process, the classification identification process, and the like, thereby discriminating and sorting the sorting target S0 (the discrimination processing and the sorting processing).

The sorting apparatus 201 according to the present embodiment is configured and functions in the manner described with reference to FIG. 7 and the like (FIGS. 1 to 5C for the X-ray discrimination apparatus 10).

The sorting apparatus 201 according to the third embodiment and the sorting apparatus 101 according to the above-described second embodiment are partially differently configured (for example, the configuration of the conveyance portion), but similarly configured in terms of the discriminator and the sorter. Therefore, the sorting apparatus 201 according to the third embodiment also brings about advantageous effects generally similar to the sorting apparatus 101 described in the second embodiment. Therefore, the detailed descriptions of the advantageous effects thereof will be omitted here.

<Other Embodiments> The present invention is not limited to the above-described embodiments and can also be embodied with various modifications added thereto as necessary within a range that can comply with the spirit of the present invention, and any of such modifications is also included in the technical scope of the present invention.

The above-described embodiments have been described assuming that the sorting target is nuts, beans, a kernel, or the like, but the present invention is not limited to this configuration. Therefore, for example, the sorting target may be a vegetable, confectionery, processed food, or the like.

Further, the above-described embodiments have been described assuming that the electromagnetic wave is an X-ray, but the present invention is not limited to this configuration. Therefore, the electromagnetic wave may be, for example, an ultraviolet ray, a visible light ray, a near-infrared ray, an infrared ray, a microwave, or the like.

Further, the above-described embodiments have been described assuming that the "inference model" forming the discrimination method, the sorting method, and the sorting apparatus is the inference model acquired using deep learning, but the present invention is not limited to this configuration. Therefore, for example, the "inference model" may be constructed using a learning program formed by combining at least one or more of a support vector machine (SVM), a naive Bayes classifier, logistic regression, a random forest, a neural network, deep learning, the k-nearest neighbors algorithm, AdaBoost, bagging, C4.5, the kernel method, stochastic gradient descent, Lasso regression, Ridge regression, Elastic Net, the interpolation method, and collaborative filtering.

Further, the above-described embodiments have been described assuming that the inference model is constructed using the X-ray discriminator forming a part of the sorting apparatus (assuming that a part of the sorting apparatus including the X-ray discriminator functions as the machine learning apparatus), but the present invention is not limited to this configuration. Therefore, for example, the present invention may be configured in such a manner that the machine learning apparatus is formed using an X-ray discriminator or the like provided outside the sorting apparatus, the inference model is constructed using this machine learning apparatus outside the sorting apparatus, and the constructed inference model is installed in the sorting apparatus.

Further, the above-described embodiments have been described assuming that the inference model is constructed using the X-ray discriminator forming a part of the sorting apparatus, and the PC, but the present invention is not limited to this configuration. Therefore, for example, the inference model may be constructed by collecting required imaging information using the X-ray discriminator forming the sorting apparatus or an externally provided equivalent apparatus and using the collected imaging information and the like and a function inside the sorting apparatus. In other words, the present invention may be configured in such a manner that the machine learning apparatus is formed by the sorting apparatus itself or a part thereof, the inference model is, for example, constructed and/or updated inside the sorting apparatus, and the required inference model is installed in the sorting apparatus (the discriminator included therein) as appropriate.

Further, the above-described embodiments have been described assuming that the inference model is constructed, and the discrimination processing and the sorting processing for the sorting target are performed using the constructed inference model, but the present invention is not limited to this configuration. Therefore, for example, the present invention may use the "adjacency information between sorting targets" and the "classification information of the sorting target", which are the imaging information, when performing the discrimination processing and the sorting processing, without constructing the inference model. In other words, the present invention may be configured to appropriately perform the discrimination processing and the sorting processing for an acceptable product or a defective product with respect to the sorting target by setting predetermined threshold value information regarding these "adjacency information between sorting targets" and "classification information of the sorting target" and comparing this threshold value information and the "adjacency information between sorting targets" and "classification information of the sorting target" regarding the sorting target.

Further, the present invention may use the "adjacency information between sorting targets", the "classification information of the sorting target", and the "background information of the sorting target", which are the imaging information, when performing the discrimination processing and the sorting processing, without constructing the inference model. In other words, the present invention may be configured to appropriately perform the discrimination processing and the sorting processing for an acceptable product or a defective product with respect to the sorting target by also setting predetermined threshold value information regarding the "background information of the sorting target" in addition to the above-described "adjacency information between sorting targets" and "classification information of the sorting target", and comparing this threshold value information and the "adjacency information between sorting targets", the "classification information of the sorting target", and the "background information of the sorting target" regarding the sorting target.

Further, the above-described embodiments have been described assuming that the trimming processing is performed according to the size of 40×40 pixels in the trimming processing process when generating the learning images (the learning information), but the present invention is not limited to this configuration. The size of the trimming at the time of the trimming processing process is a size approximately equal to the size of a single body of the sorting target and is appropriately determined according to the shape of the sorting target as described above. Therefore, for example, the trimming processing process may be performed according to a size such as 32×32 pixels or 64×64 pixels according to the size and the shape of a single body of the sorting target.

Further, the above-described embodiments have been described assuming that the classification information is the acceptable portion information and the defective portion information, but the present invention is not limited to this configuration, and various kinds of information different from the acceptable portion and the defective portion can be employed as the classification information. Therefore, for example, a classification for each quality level of a predetermined sorting target or a classification regarding the kind of the sorting target can also be used as the classification information.

Further, at least a part of the functions of the CPU 172, the X-ray image processor 173, the image processor 174, and the determination result combination mechanism 175 may be realized by a controller that controls at least a part of the operation of the sorting apparatus 10. The same also applies to at least a part of the functions of the CPU 272, the X-ray image processor 273, the image processor 274, and the determination result combination mechanism 275. In this case, each function of the controller may be realized by execution of a predetermined program by the CPU, may be realized by a dedicated circuit, or may be realized by a combination of them. Further, a single controller may be used. Alternatively, a plurality of controllers may be used to distribute a plurality of functions and a plurality of required functions may be realized by the whole of the plurality of controllers.

Further, in the case where the discrimination processing and the sorting processing are performed without constructing the inference model, for example, respective pluralities of templates may be prepared for determining the "adjacency information between sorting targets" and for determining the "classification information of the sorting target". Such templates may be the same as or similar to the first labeling image 331 to the sixth labeling image 336 illustrated in FIG. 3C. In the case where the templates are used, the "adjacency information between sorting targets" and the "classification information of the sorting target" may be determined by carrying out template matching in the image processing, calculating a correlation coefficient between each template and the raw image 510 (or the image after the normalization processing is performed on the raw image 510) with respect to each of the "adjacency information between sorting targets" and the "classification information of the sorting target", and using this correlation coefficient.

INDUSTRIAL APPLICABILITY

The present disclosure has been contrived with the aim of providing a method for discriminating a sorting target that appropriately perceives a state of the sorting target itself and a relationship between a plurality of sorting targets and appropriately discriminates the sorting target based on the perceived information, and also providing a method and an apparatus for sorting the sorting target that appropriately discriminate and sort the sorting target based on the discrimination information.

Conventionally, apparatuses utilizing an X-ray or the like to, for example, inspect a shape inside an inspection target have been known, but basically have extracted an internally abnormally shaped portion or the like by binarizing shades of gray in a grayscale image not having color information. However, such conventional apparatuses have had difficulty in clearly recognizing an abnormal portion of the inspection target itself and a portion around the inspection target (for example, an adjacency state between inspection targets).

To solve such a problem, for example, the discrimination method according to the present disclosure is configured in the following manner.

The method for discriminating the sorting target according to the present embodiments includes the transfer process of transferring the sorting target, the imaging process of imaging the sorting target during the transfer process, and the discrimination process of discriminating the sorting target based on the imaging information acquired in the imaging process. The discrimination process is performed using the inference model generated based on the learning information regarding the sorting target. The learning information includes the adjacency information between sorting targets, the classification information of the sorting target, and the background information of the sorting target (the background labeling portion SP4). The discrimination process includes discriminating the sorting target using the imaging information and the inference model.

Further, the sorting method and the sorting apparatus according to the present disclosure are formed using the above-described discrimination method.

In this manner, the discrimination method, the sorting method, and the sorting apparatus according to the present disclosure appropriately solve the problem(s) with the existing apparatuses (the conventional techniques), and therefore are considered to be highly industrially applicable.

DESCRIPTION OF THE REFERENCE NUMERALS

10 X-ray discriminator (X-ray discrimination apparatus, discrimination apparatus, imaging portion)
11 X-ray generation portion (X-ray generation portion included in an imaging portion)
11*a* X-ray
12 X-ray detection portion (X-ray detection portion included in the imaging portion)
91 conveyance path (transfer portion, conveyance path included in the transfer portion)
101 sorting apparatus (belt-type sorting apparatus)
120 sorting target feeding portion
130 conveyance portion (transfer portion)
131 conveyance belt (transfer portion, conveyance belt included in the transfer portion, conveyance path)
132, 133 roller
134 driving motor
150 optical detection portion
151 light-receiving portion
151A first light-receiving portion
151B second light-receiving portion
153 light-emitting portion
155 background portion
160 sorting portion (sorter)
161 nozzle portion
162 electromagnetic valve
171 touch panel
172 CPU (central processing unit)
173 X-ray image processor
174 image processor
175 determination result combination mechanism
181 acceptable product containing portion
182 defective product discharge portion
201 sorting apparatus (chute-type sorting apparatus)
220 sorting target feeding portion
230 chute (conveyance portion, transfer portion)
231 inclined plate portion (transfer portion, inclined plate portion included in the transfer portion, conveyance path)
250 optical detection portion
251 light-receiving portion
251A first light-receiving portion
251B second light-receiving portion
253 light-emitting portion
255 background portion
260 sorting portion (sorter)
261 nozzle portion
262 electromagnetic valve
271 touch panel
272 CPU (central processing unit)
273 X-ray image processor
274 image processor
275 determination result combination mechanism
281 acceptable product containing portion
282 defective product containing portion
310 raw image
320 trimmed image group
321 to 326 first trimmed image to sixth trimmed image (trimmed images)
330 labeling image group (learning images, learning information)
331 to 336 first labeling image to sixth labeling image (labeling images) (learning images, learning information)
510 raw image (imaging information)
520 inference result image
530 post-filter processing image
S, SS, S0 sorting target
S1 acceptable portion information (classification information)
S2 defective portion information (deficiency information) (classification information)
S3 adjacency information
S4 background information
SP1, SSP1 acceptable portion labeling portion (classification information)
SP2, SSP2 defective portion labeling portion (classification information)
SP3, SSP3 adjacency labeling portion (adjacency information)
SP4, SSP4 background labeling portion (background information)
C1 acceptable portion (acceptable portion labeling portion, classification information)
C2 defective portion (defective portion labeling portion, classification information)
C4 background portion (background labeling portion, background information)
CA, CB sorting target

What is claimed is:

1. A method for discriminating a sorting target, the method comprising:

transferring the sorting target;

imaging the sorting target during the transferring; and discriminating the sorting target based on imaging information acquired in the imaging, wherein the imaging information includes a labeled image having:

a) classification information acquired by performing labeling processing with respect to an acceptable portion or a defective portion of the sorting target, and b) adjacency information acquired by performing labeling processing to assign, without processing for cutting out an object, an adjacency portion to a portion of the labeled image that satisfies an adjacency distance defining a distance between adjacent sorting targets or an adjacency ratio defining a ratio of the distance between sorting targets to a size of the sorting target.

2. The method for discriminating the sorting target according to claim 1, wherein the imaging information further includes background information of the sorting target.

3. The method for discriminating the sorting target according to claim 2, wherein the discriminating is performed using an inference model generated based on learning information regarding the sorting target, and the learning information includes the adjacency information between the sorting targets and the classification information of the sorting target, and the discriminating includes discriminating the sorting target using the imaging information and the inference model.

4. A method for sorting a sorting target, the method comprising:

the method for discriminating the sorting target according to claim 3; and sorting the sorting target based on discrimination information acquired in the discriminating.

5. A method for sorting a sorting target, the method comprising:

the method for discriminating the sorting target according to claim 2; and sorting the sorting target based on discrimination information acquired in the discriminating.

6. The method for discriminating the sorting target according to claim 1, wherein the discriminating is performed using an inference model generated based on learning information regarding the sorting target, and the learning information includes the adjacency information between the sorting targets and the classification information of the sorting target, and the discriminating includes discriminating the sorting target using the imaging information and the inference model.

7. A method for sorting a sorting target, the method comprising:

the method for discriminating the sorting target according to claim 6; and sorting the sorting target based on discrimination information acquired in the discriminating.

8. A method for sorting a sorting target, the method comprising:

the method for discriminating the sorting target according to claim 1; and sorting the sorting target based on discrimination information acquired in the discriminating.

9. A sorting apparatus comprising:

a transfer portion configured to transfer a sorting target;

an imaging portion configured to image the sorting target during the transfer by the transfer portion;

a discrimination portion configured to discriminate the sorting target based on imaging information acquired by the imaging portion; and a sorting portion configured to sort the sorting target based on discrimination information acquired by the discrimination means, wherein the imaging information includes a labeled image having:

a) classification information acquired by performing labeling processing with respect to an acceptable portion or a defective portion of the sorting target, and b) adjacency information acquired by performing labeling processing to assign, without processing for cutting out an object, an adjacency portion to a portion of the labeled image that satisfies an adjacency distance defining a distance between adjacent sorting targets or an adjacency ratio defining a ratio of the distance between sorting targets to a size of the sorting target.

10. The sorting apparatus according to claim 9, wherein the discrimination portion includes an inference model generated based on learning information regarding the sorting target, and the learning information includes the adjacency information between the sorting targets and the classification information of the sorting target, and the discrimination portion is further configured to discriminate the sorting target using the imaging information and the inference model.

11. A discrimination apparatus comprising:

a transfer portion configured to transfer a plurality of discrimination targets;

an imaging portion configured to image the plurality of discrimination targets during the transfer by the transfer portion; and a discrimination portion configured to discriminate the individual discrimination targets based on imaging information acquired by the imaging portion, wherein the imaging information includes a labeled image having:

a) classification information acquired by performing labeling processing with respect to an acceptable portion or a defective portion of the discrimination target, and b) adjacency information acquired by performing labeling processing to assign, without processing for cutting out an object, an adjacency portion to a portion of the labeled image that satisfies an adjacency distance defining a distance between adjacent discrimination targets or an adjacency ratio defining a ratio of the distance between discrimination targets to a size of the discrimination target.

* * * * *